(12) United States Patent
Furuya et al.

(10) Patent No.: US 6,329,388 B2
(45) Date of Patent: Dec. 11, 2001

(54) THIENOPYRIDINE COMPOUNDS, THEIR PRODUCTION AND USE

(75) Inventors: Shuichi Furuya; Nobuo Choh; Nobuhiro Suzuki; Takashi Imada, all of Tsukuba (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/736,641

(22) Filed: Dec. 14, 2000

Related U.S. Application Data

(62) Division of application No. 09/420,358, filed on Oct. 18, 1999, which is a continuation of application No. 09/402,206, filed on Sep. 30, 1999, now Pat. No. 6,262,267.

(30) Foreign Application Priority Data

Jun. 26, 1998 (JP) .................................................. 10-181263
Nov. 24, 1998 (JP) .................................................. 10-333004

(51) Int. Cl.$^7$ ........................ A61K 31/435; C07D 495/04
(52) U.S. Cl. ............................................. 514/301; 546/114
(58) Field of Search .............................. 546/114; 514/301

(56) References Cited

U.S. PATENT DOCUMENTS 5,817,819 * 10/1998 Furuya et al. ........................ 546/114

FOREIGN PATENT DOCUMENTS

| 781774 | * 2/1997 | (EP) . |
| 09-169766 | 6/1997 | (JP) . |
| WO 95/28405 | 10/1995 | (WO) . |
| WO 97/41126 | 11/1997 | (WO) . |

* cited by examiner

*Primary Examiner*—Bernard Dentz
(74) *Attorney, Agent, or Firm*—Mark Chao; Elaine M. Ramesh

(57) ABSTRACT

The compounds of the present invention possess excellent gonadotropin-releasing hormone antagonizing activity, and is useful for preventing or treating sex hormone-dependent diseases, e.g., sex hormone-dependent cancers (e.g., prostatic cancer, uterine cancer, breast cancer, pituitary tumor), prostatic hypertrophy, hysteromyoma, endometriosis, precocious puberty, amenorrhea syndrome, multilocular ovary syndrome, pimples etc, or as a pregnancy regulator (e.g., contraceptive), infertility remedy or menstruation regulator.

17 Claims, 1 Drawing Sheet

THIENOPYRIDINE COMPOUNDS, THEIR PRODUCTION AND USE

This application is a divisional of U.S. patent application Ser. No. 09/420,358, filed Oct. 18, 1999, which was a continuation of U.S. patent application Ser. No. 09/402,206, filed Sep. 30, 1999 now U.S. Pat. No. 6,262,267, which was the National Phase filing of Intentional Patent Application No. PCT/JP99/033790, filed Jun. 24, 1999.

TECHNICAL FIELD

The present invention relates to thieno[2, 3-b]pyridine derivatives exhibiting gonadotropin releasing hormone (GnRH) antagonizing activity, their production and use.

BACKGROUND ART

The secretion of hypophysial anterior lobe hormone is regulated by the peripheral hormone secreted by each target organ and the secretion-promoting or secretion-suppressing hormone secreted by the hypothalamus, which is the center superior to the hypophysial anterior lobe, and this group of hormones hereinafter generically referred to as hypothalamic hormone in this specification. To date, nine hypothalamic hormones have been identified, for example, thyroid-stimulating hormone-releasing hormone (TRH), and gonadotropin releasing hormone [GnRH, also known as luteinizing hormone releasing hormone (LH-RH)], etc. It is conjectured that these hypothalamic hormones exhibit their hormone actions etc. via receptors assumed to be present in the hypophysial anterior lobe, and analyses of receptor genes specific to these hormones, including humans, are ongoing. Antagonists or agonists that act specifically and selectively on these receptors would therefore regulate the action of hypothalamic hormones and hence regulate the secretion of hypophysial anterior lobe hormone. As a result, such antagonists or agonists are expected to prevent or treat diseases depending on these hypophysial anterior lobe hormone.

Known compounds possessing GnRH-antagonizing activity include GnRH-derived linear peptides (U.S. Pat. No. 5,140,009 and U.S. Pat. No. 5,171,835), a cyclic hexapeptide derivative (JP-A-61-191698), a bicyclic peptide derivative [Journal of Medicinal Chemistry, Vol. 36, pp. 3265–3273 (1993)], and so forth. Non-peptide compounds possessing GnRH-antagonizing activity include compounds described in WO 95/28405, WO 97/14697, WO 97/14682, WO 97/41126 and so forth.

Peptide compounds pose a large number of problems to be resolved with respect to oral absorbability, dosage form, dose volume, drug stability, sustained action, metabolic stability etc. There is strong demand for an oral GnRH antagonist, especially one based on a non-peptide compound, that has excellent therapeutic effect on hormone-dependent cancers, e.g., prostatic cancer, endometriosis, precocious puberty etc., and that does not show transient hypophysial-gonadotropic action (acute action).

DISCLOSURE OF INVENTION

Figure 1:
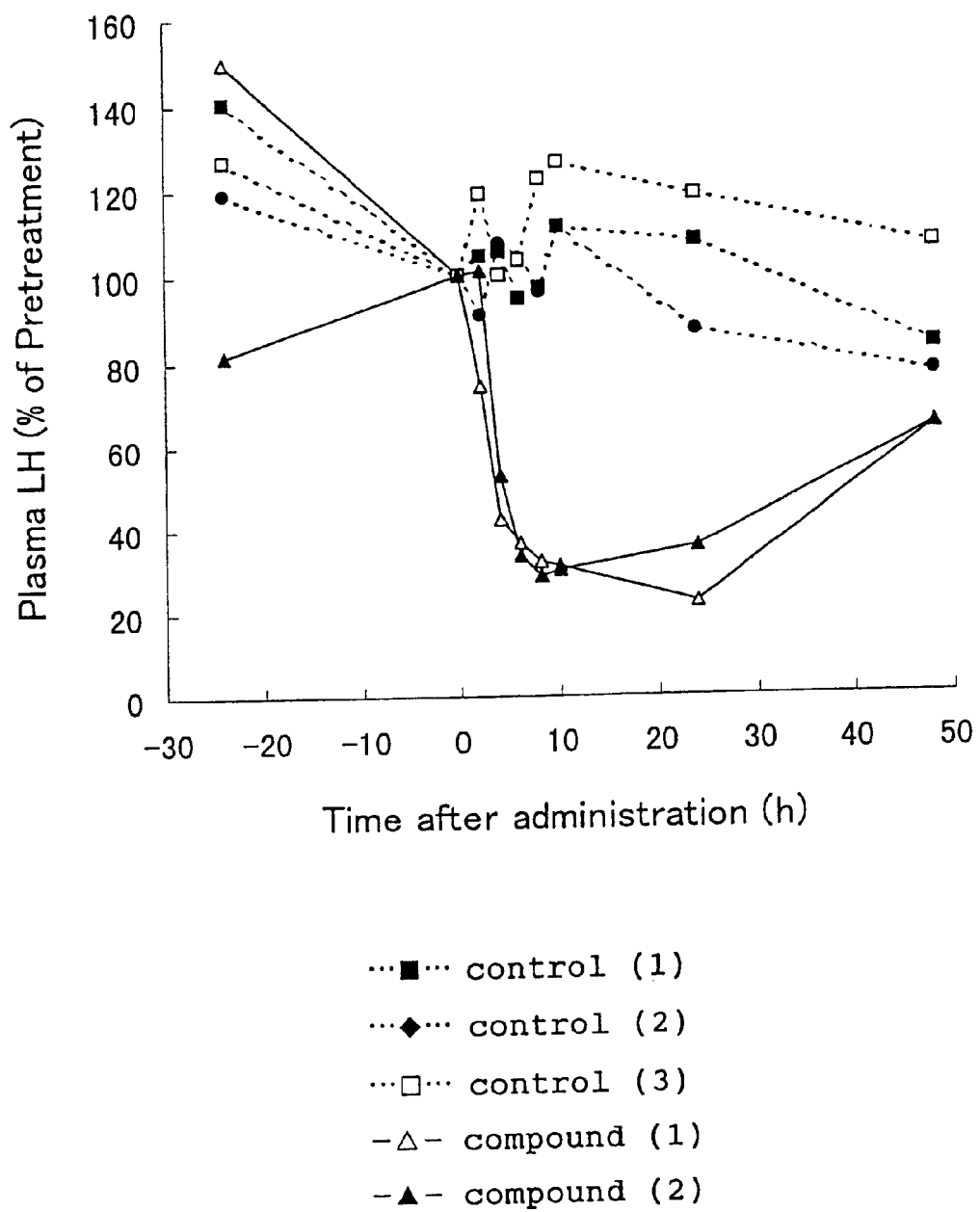
FIG. 1 is a diagrammatic representation of the ameliorating effect of suppression of plasma LH concentrations in castrated monkeys after oral administration of the compound of the following Example 1–2, in which ■ represents control (1) (vehicle), ♦ represents control (2) (vehicle), □ represents control (3) (vehicle), -Δ- represents compound(1) [thetestanimal administered the compound of Ex. No. 1–2] and -▲- represents compound (2) [the test animal administered the compound of Ex. No. 1–2].

The present inventors produced various thieno pyridine derivatives, investigated their actions, and found that some compounds possess excellent GnRH-antagonizing activity. The inventors have conducted further investigation based on this finding, and developed the present invention.

Accordingly, the present invention relates to:

[1] a compound of the formula:

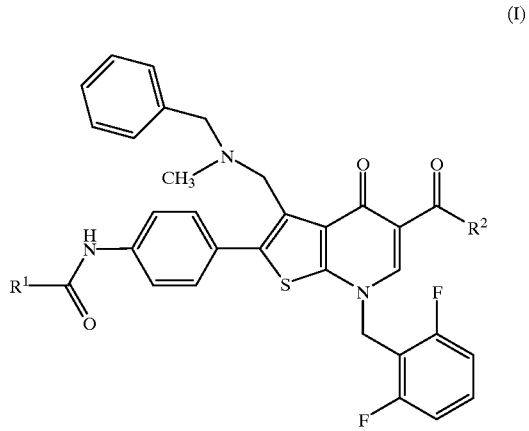

(I)

wherein $R^1$ represents a $C_{1-7}$ alkyl group which may be substituted, a $C_{3-7}$ cycloalkyl group which may be substituted, a $C_{1-6}$ alkoxyamino group which may be substituted or a hydroxyamino group which may be substituted; and $R^2$ represents a $C_{1-7}$ alkyl group which may be substituted or a phenyl group which may be substituted; when $R^1$ is an unsubstituted $C_{1-7}$ alkyl group, then $R^2$ is a substituted $C_{1-7}$ alkyl group or a substituted phenyl group, or a salt thereof [hereinafter sometimes referred to briefly as compound (I)];

[2] a compound of the above (1) or a salt thereof, wherein $R^1$ is (1) a $C_{1-7}$ alkyl group which may be substituted by 1 to 5 substituents selected from the group consisting of (i) hydroxy, (ii) $C_{1-7}$ acyloxy, (iii) amino which may be substituted by 1 or 2 substituents selected from the group consisting of $C_{1-6}$ alkoxy-carbonyl, benzyloxycarbonyl, $C_{1-3}$ acyl, $C_{1-3}$ alkylsulfonyl and $C_{1-3}$ alkyl, (iv) $C_{1-0}$ alkoxy which may be substituted by 1 to 3 substituents selected from the group consisting of $C_{3-7}$ cycloalkyloxy-carbonyl and $C_{1-3}$ alkoxy and (v) $C_{1-6}$ alkoxy-carbonyl, (2) a $C_{3-7}$ cycloalkyl group which may be substituted by 1 to 3 substituents selected from the group consisting of (i) hydroxy, (ii) $C_{1-7}$ acyloxy, (iii) amino which may be substituted by 1 or 2 substituents selected from the group consisting of $C_{1-6}$ alkoxy-carbonyl, benzyloxycarbonyl, $C_{1-3}$ acyl, $C_{1-3}$ alkylsulfonyl and $C_{1-3}$ alkyl, (iv) $C_{1-10}$ alkoxy which may be substituted by 1 to 3 substituents selected from the group consisting of $C_{3-7}$ cycloalkyloxy-carbonyl and $C_{1-3}$ alkoxy and (v) $C_{1-6}$ alkoxy-carbonyl, (3) a $C_{1-6}$ alkoxyamino group which may be substituted by 1 to 5 substituents selected from the group consisting of (i) hydroxy, (ii) $C_{1-7}$ acyloxy, (iii) amino which may be substituted by 1 or 2 substituents selected from the group consisting of $C_{1-6}$ alkoxy-carbonyl, benzyloxycarbonyl, $C_{1-3}$ acyl, $C_{1-3}$ alkylsulfonyl and $C_{1-3}$ alkyl, (iv) $C_{1-3}$ alkoxy which may be substituted by 1 to 3 substituents selected from the group consisting of $C_{3-7}$ cycloalkyloxy-carbonyl and $C_{1-3}$ alkoxy and (v) $C_{1-6}$ alkoxy-carbonyl, or
(4) a hydroxyamino group which may be substituted by 1 or 2 substituents selected from the group consisting of (i) $C_{1-7}$ acyloxy, (ii) amino which may be substituted by 1 or 2 substituents selected from the group consisting of $C_{1-6}$ alkoxy-carbonyl, benzyloxycarbonyl, $C_{1-3}$ acyl, $C_{1-3}$ alkylsulfonyl and $C_{1-3}$ alkyl, (iii) $C_{1-10}$ alkoxy which may be substituted by 1 to 3 substituents selected from the group consisting of $C_{3-7}$ cycloalkyloxy-carbonyl and $C_{1-3}$ alkoxy and
(iv) $C_{1-6}$ alkyl; and
$R^2$ is (1) a $C_{1-7}$ alkyl group which may be substituted by 1 to 5 substituents selected from the group consisting of (i) hydroxy, (ii) $C_{1-7}$ acyloxy, (iii) amino which may be substituted by 1 or 2 substituents selected from the group consisting of $C_{1-6}$ alkoxy-carbonyl, benzyloxycarbonyl, $C_{1-3}$ acyl, $C_{1-3}$ alkylsulfonyl and $C_{1-3}$ alkyl, (iv) $C_{1-10}$ alkoxy which may be substituted by 1 to 3 substituents selected from the group consisting of $C_{3-7}$ cycloalkyloxy-carbonyl and $C_{1-3}$ alkoxy and (v) $C_{1-6}$ alkoxy-carbonyl, or
(2) a phenyl group which may be substituted by 1 to 5 substituents selected from the group consisting of halogen, $C_{1-3}$ alkyl and $C_{1-3}$ alkoxy;

[3] a compound of the above (1) or a salt thereof, wherein $R^1$ is a $C_{1-7}$ alkyl group which may be substituted or a $C_{3-7}$ cycloalkyl group which may be substituted;

[4] a compound of the above (1) or a salt thereof, wherein $R^1$ is a substituted branched $C_{3-7}$ alkyl group or a substituted $C_{3-7}$ cycloalkyl group;

[5] a compound of the above (1) or a salt thereof, wherein $R^1$ is a $C_{1-7}$ alkyl group substituted by hydroxy or a $C_{3-7}$ cycloalkyl group substituted by hydroxy;

[6] a compound of the above (1) or a salt thereof, wherein $R^1$ is a substituted $C_{3-7}$ cycloalkyl group;

[7] a compound of the above (1) or a salt thereof, wherein $R^1$ is a cyclopropyl group which may be substituted by hydroxy;

[8] a compound of the above (1) or a salt thereof, wherein $R^2$ is a branched $C_{3-7}$ alkyl group which may be substituted;

[9] a compound of the above (1) or a salt thereof, wherein $R^2$ is a phenyl group which may be substituted;

[10] a compound of the above (1) or a salt thereof, wherein $R^2$ is a phenyl group;

[11] a compound of the above (1) or a salt thereof, wherein $R^1$ is a $C_{3-7}$ cycloalkyl group and $R^2$ is a $C_{1-6}$ alkyl group;

[12] a compound of the above (1) or a salt thereof, wherein $R^1$ is (1) a $C_{1-4}$ alkyl group substituted by 1 or 2 hydroxy, (2) a $C_{3-7}$ cycloalkyl group substituted by hydroxy, or (3) a $C_{1-3}$ alkoxyamino group; and $R^2$ is an isopropyl group or a phenyl group;

[13] a compound of the above (1) or a salt thereof, wherein $R^1$ is (1) a $C_{1-7}$ alkyl group which may be substituted by 1 or 2 substituents selected from the group consisting of hydroxy, $C_{1-3}$ alkyl-carbonyloxy, amino, benzyloxycarbonylamino, $C_{1-3}$ alkoxy, $C_{1-3}$ alkoxy-$C_{1-3}$ alkoxy and $C_{1-3}$ alkoxy-carbonyl, (2) a $C_{3-7}$ cycloalkyl group which may be substituted by a hydroxy or a $C_{1-3}$ alkyl-carbonyloxy. or (3) a $C_{1-3}$ alkoxyamino group; and $R^2$ is (1) an isopropyl group which may be substituted by a hydroxy or (2) a phenyl group;

[14] 3-(N-benzyl-N-methylaminomethyl)-4,7-dihydro-5-isobutyryl-7-(2,6-difluorobenzyl)-2-(4-cyclopropanecarbonylaminophenyl)-4-oxothieno[2,3-b]pyridine or a salt thereof;

[15] 3-(N-benzyl-N-methylaminomethyl)-4,7-dihydro-5-isobutyryl-7-(2,6-difluorobenzyl)-2-[4-(3-hydroxy-2-methylpropionylamino)phenyl]-4-oxothieno[2,3-b]pyridine or a salt thereof;

[16] 3-(N-benzyl-N-methylaminomethyl)-4,7-dihydro-5-isobutyryl-7-(2,6-difluorobenzyl)-2-[4-[(1-hydroxycyclopropyl)carbonylamino]phenyl]-4-oxothieno[2,3-b]pyridine or a salt thereof;

[17] 3-(N-benzyl-N-methylaminomethyl)-5-benzoyl-7-(2,6-difluorobenzyl)-4,7-dihydro-2-[4-[(1-hydroxycyclopropyl)carbonylamino]phenyl]-4-oxothieno[2,3-bipyridine or a salt thereof;

[18] a process for producing a compound of the above [1] or a salt thereof, which comprises reacting a compound of the formula:

(II)

wherein $R^2$ represents a $C_{1-7}$ alkyl group which may be substituted or a phenyl group which may be substituted, or a salt thereof [hereinafter sometimes referred to briefly as compound (II)], with
i) a compound of the formula:

$R^{1a}COOH$ wherein $R^{1a}$ represents a $C_{1-7}$ alkyl group which may be substituted or a $C_{3-7}$ cycloalkyl group which may be substituted, or a salt thereof or a reactive derivative thereof; or ii) carbonyldiimidazole, phosgene or a chloroformate, followed by reacting with a compound of the formula:

$R^{1b}_H$ wherein $R^{1b}$ represents a $C_{1-6}$ alkoxyamino group which may be substituted or a hydroxyamino group which may be substituted, or a salt thereof;

19] a process for producing a compound of the above [3] or a salt thereof, which comprises reacting compound (II) with a compound of the formula:

$R^{1a}COOH$ wherein $R^{la}$ represents a $C_{1-7}$ alkyl group which may be substituted or a $C_{3-7}$ cycloalkyl group which may be substituted, or a salt thereof or a reactive derivative thereof;

[20] a pharmaceutical composition which comprises a compound of the above (1) or a salt thereof;

[21] a pharmaceutical composition of the above (20) which is for antagonizing gonadotropin-releasing hormone;

[22] a pharmaceutical composition of the above (21) which is for preventing or treating a sex hormone dependent disease:

[23] a method for antagonizing gonadotropin-releasing hormone in a mammal in need thereof which comprises administering to said mammal an effective amount of a compound of the above (1) or a salt thereof with a pharmaceutically acceptable excipient, carrier or diluent;

[24] use of a compound of the above (1) or a salt thereof for manufacturing a pharmaceutical composition for antagonizing gonadotropin-releasing hormone, and so forth.

Each symbol in the above formulae is hereinafter described in more detail.

The "$C_{1-7}$ alkyl group" of the "$C_{1-7}$ alkyl group which may be substituted" for $R^1$ includes, for example, a straight-chain $C_{1-7}$ alkyl group such as methyl, ethyl, propyl, butyl, pentyl, hexyl, heptyl, etc.; a branched $C_{3-7}$ alkyl group such as isopropyl, isobutyl, sec-butyl, tert-butyl, isopentyl, neopentyl, etc., and so forth. Among others, preferred is a branched $C_{3-7}$ alkyl group. More preferred is isopropyl.

The "substituents" of the "$C_{1-7}$ alkyl group which may be substituted" for $R^1$ include, for example, (i) hydroxy, (ii) $C_{1-7}$ acyloxy (e.g., $C_{1-6}$ alkyl-carbonyloxy such as acetoxy, propionyloxy, etc.; benzoyloxy etc.), (iii) amino which may be substituted by 1 or 2 substituents selected from the group consisting of $C_{1-6}$ alkoxy-carbonyl (e.g., methoxycarbonyl, ethoxycarbonyl, tert-butoxycarbonyl, etc.), benzyloxycarbonyl, $C_{1-3}$ acyl (e.g., $C_{1-2}$ alkyl-carbonyl such as acetyl, propionyl, etc.), $C_{1-3}$ alkylsulfonyl (e.g., methanesulfonyl etc.) and $C_{1-3}$ alkyl (e.g., methyl, ethyl, etc.), etc. [e.g.; amino, methoxycarbonylamino, ethoxycarbonylamino, tert-butoxycarbonyl benzyloxycarbonylamino, acetylamino, methanesulfonylamino, methylamino, dimethylamino, etc.), (iv) $C_{1-10}$ (preferably $C_{1-4}$) alkoxy which may be substituted by 1 to 3 substituents selected from the group consisting of $C_{3-7}$ cycloalkyloxycarbonyl (e.g., cyclohexyloxycarbonyloxy, etc.) and $C_{1-3}$ alkoxy (e.g., methoxy, ethoxy, etc.) [e.g.; methoxy, ethoxy, propoxy, tert-butoxy, cyclohexyloxycarbonyloxy-1-ethoxy, methoxymethoxy, ethoxymethoxy, etc.], (v) $C_{1-6}$ alkoxycarbonyl (e.g., methoxycarbonyl, ethoxycarbonyl, propoxycarbonyl, etc.), and so forth. Among others, preferred is hydroxy.

The "$C_{1-7}$ alkyl group" may have 1 to 5, preferably 1 to 3 substituents as mentioned above at possible positions and, when the number of substituents is two or more, those substituents may be the same as or different from one another.

The "$C_{3-7}$ cycloalkyl group" of the "$C_{3-7}$ cycloalkyl group which may be substituted" for $R^1$ includes, for example, cyclopropyl, cyclobutyl, cyclopentyl, cyclohexyl, cycloheptyl, etc. Among others, preferred is cyclopropyl.

The "substituents" of the "$C_{3-7}$ cycloalkyl group which may be substituted" for $R^1$ are the same as those mentioned above for the "substituents" of the "$C_{1-7}$ alkyl group which may be substituted" for $R^1$. The number of substituents is 1 to 3. When the number of substituents is two or more, those substituents may be the same as or different from one another.

The "$C_{1-6}$ alkoxyamino group" of the "$C_{1-6}$ alkoxyamino group which may be substituted" for $R^1$ includes, for example, mono- or di-$C_{1-6}$ alkoxyamino (e.g., methoxyamino, ethoxyamino, dimethoxyamino, diethoxyamino, ethoxymethoxyamino, etc.), etc. Among others, preferred is mono-$C_{1-3}$ alkoxyamino (e.g., methoxyamino, etc.).

The "substituents" of the "$C_{1-6}$ alkoxyamino group which may be substituted" for $R^1$ and their number are the same as those mentioned above for the "substituents" of the $C_{1-7}$ alkylgroup which may be substituted"for $R^1$. When the number of substituents is two or more, those substituents may be the same as or different from one another. The "$C_{1-6}$ alkoxy" or the "nitrogen atom of an amino group" of the $C_{1-6}$ alkoxyamino group may be substituted by the above "substituents".

Such "$C_{1-6}$ alkoxyamino group which may be substituted" is exemplified by methoxyamino, N-methyl-N-methoxyamino, N-ethyl-N-methoxyamino, ethoxyamino, dimethoxyamino, diethoxyamino, ethoxymethoxyamino, etc. Preferred is $C_{1-3}$ alkoxyamino, N-$C_{1-3}$ alkyl-N-$C_{1-3}$ alkoxyamino, etc.

The "substituents" of the "hydroxyamino group which may be substituted" for $R^1$ may be located on the "hydroxy group" of the hydroxyamino group or the "nitrogen atom of an amino group" of the hydroxyamino group. Such "substituents" on the "hydroxy group" include, for example, (i) $C_{1-7}$ acyloxy (e.g., $C_{1-6}$ alkyl-carbonyloxy such as acetoxy, propionyloxy, etc.; benzoyloxy etc.), (ii) amino which may be substituted by 1 or 2 substituents selected from the group consisting of $C_{1-6}$ alkoxy-carbonyl (e.g., methoxycarbonyl, ethoxycarbonyl, tert-butoxycarbonyl, etc.), benzyloxycarbonyl, $C_{1-3}$ acyl (e.g., $C_{1-2}$ alkyl-carbonyl such as acetyl, propionyl, etc.), $C_{1-3}$ alkylsulfonyl (e.g., methanesulfonyl etc.) and $C_{1-3}$ alkyl (e.g., methyl, ethyl, etc.), etc. [e.g.; amino, methoxycarbonylamino, ethoxycarbonylamino, tert-butoxycarbonyl benzyloxycarbonylamino, acetylamino, methanesulfonylamino, methylamino, dimethylamino, etc.], (iii) $C_{1-10}$ (preferably $C_{1-4}$) alkoxy which may be substituted by 1 to 3 substituents selected from the group consisting of $C_{3-7}$ cycloalkyloxycarbonyl (e.g., cyclohexyloxycarbonyloxy, etc.) and $C_{1-3}$ alkoxy (e.g., methoxy, ethoxy, etc.) [e.g.; methoxy, ethoxy, propoxy, tert-butoxy, cyclohexyloxycarbonyloxy-1-ethoxy, methoxymethoxy, ethoxymethoxy, etc.], and so forth. The number of substituents is 1 to 5, preferably 1 to 3. When the number of substituents is two or more, those substituents may be the same as or different from one another. Such "substituents" on the "nitrogen atom of the amino group" include, for example, (1) each group as described in the above (i) to (iii) and (2) $C_{1-6}$ alkyl (e.g., methyl, ethyl, propyl, isopropyl, butyl, isobutyl, sec-butyl, tert-butyl, pentyl, isopentyl, neopentyl, hexyl, etc. The number of substituents is 1 to 5, preferably 1 to 3. When the number of substituents is two or more, those substituents may be the same as or different from one another.

Preferable examples of the "hydroxyamino group which may be substituted" include N-$C_{1-6}$ alkyl-N-hydroxyamino (e.g., N-methyl-N-hydroxyamino, N-ethyl-N-hydroxyamino, etc.) and so forth. More preferred is N-$C_{1-3}$ alkyl-N-hydroxyamino, etc.

The "$C_{1-7}$ alkyl group" of the "$C_{1-7}$ alkyl group which may be substituted" for $R^2$ includes, for example, a straight-chain or branched $C_{1-7}$ alkyl group such as methyl, ethyl, propyl, isopropyl, butyl, isobutyl, sec-butyl, tert-butyl, pentyl, isopentyl, neopentyl, hexyl, heptyl, etc. Among others, preferred is $C_{1-3}$ alkyl (e.g., methyl, ethyl, propyl, isopropyl, etc. More preferred is isopropyl.

The "substituents" of the "$C_{1-7}$ alkyl group which may be substituted" for $R^2$ and their number are the same as those mentioned above for the "substituents" of the "$C_{1-7}$ alkyl group which may be substituted" for $R^1$. When the number of substituents is two or more, those substituents may be the same as or different from one another.

The "substituents" of the "phenyl group which may be substituted" for $R^2$ includes, for example, halogen (e.g., fluoro, chloro, bromo, iodo, etc.), $C_{1-3}$ alkyl (e.g., methyl, ethyl, propyl, isopropyl, etc.), $C_{1-3}$ alkoxy (e.g., methoxy, ethoxy, propoxy, isopropoxy, etc.), etc. Among others, preferred is halogen, more preferred is fluoro.

The "phenyl group" may have 1 to 5, preferably 1 to 3 substituents as mentioned above at possible positions and, when the number of substituents is two or more, those substituents maybe the same as or different from one another.

$R^1$ is preferably a substituted branched $C_{3-7}$ alkyl group or a substituted $C_{3-7}$ cycloalkyl group, more preferably a $C_{1-7}$ alkyl group substituted by hydroxy or a $C_{3-7}$ cycloalkyl group substituted by hydroxy. Among others, preferred is a substituted $C_{3-7}$ cycloalkyl group. Also, a $C_{1-3}$ alkyl. group which may be substituted by hydroxy, a $C_{3-7}$ cycloalkyl group which may be substituted by a hydroxy, mono-$C_{1-3}$ alkoxyamino, N-$C_{1-3}$ alkyl-N-hydroxyamino, hydroxyamino, is preferred. Especially preferably $R^1$ is (i) cyclopropyl which may be substituted by a hydroxy or (ii) methoxyamino, etc. Most preferred is cyclopropyl which may be substituted by a hydroxy group.

$R^2$ is preferably a $C_{1-7}$ alkyl group which may be substituted. More preferred is a $C_{1-3}$ alkyl group which may be substituted by a hydroxy group. Especially preferred is isopropyl. Phenyl is also preferred.

Preferable examples of compound (I) include a compound wherein, $R^1$ is a $C_{1-3}$ alkyl group which may be substituted by a hydroxy group, a $C_{3-7}$ cycloalkyl group which may be substituted by a hydroxy group or a mono-$C_{1-3}$ alkoxyamino group; and $R^2$ is a $C_{1-3}$ alkyl group, or a salt thereof.

More preferred is a compound wherein $R^1$ is (1) a $C_{1-4}$ alkyl group substituted by 1 or 2 hydroxy, (2) a $C_{3-7}$ cycloalkyl group substituted by hydroxy, or (3) a $C_{1-3}$ alkoxyamino group; and $R^2$ is an isopropyl group or a phenyl group, or a salt thereof.

A compound wherein $R^1$ is (1) a $C_{1-7}$ alkyl group which may be substituted by 1 or 2 substituents selected from the group consisting of hydroxy, $C_{1-3}$ alkyl-carbonyloxy, amino, benzyloxycarbonylamino, $C_{1-3}$ alkoxy, $C_{1-3}$ alkoxy-$C_{1-3}$ alkoxy and $C_{1-3}$ alkoxy-carbonyl, (2) a $C_{3-7}$ cycloalkyl group which may be substituted by a hydroxy group or a $C_{1-3}$ alkyl-carbonyloxy, or (3) a $C_{1-3}$ alkoxyamino group; and $R^2$ is (1) an isopropyl group which may be substituted by a hydroxy group or (2) a phenyl group, or salt thereof is also preferred.

As compound (I), concretely mentioned are
3-(N-benzyl-N-methylaminomethyl)-4,7-dihydro-5-isobutyryl-7-(2,6-difluorobenzyl)-2-(4-cyclopropanecarbonylaminophenyl)-4-oxothieno[2,3-b]pyridine or a salt thereof,
5-benzoyl-3-(N-benzyl-N-methylaminomethyl)-7-(2,6-difluorobenzyl)-4,7-dihydro-4-oxo-2-[4-(3-hydroxy-2-methylpropionylamino)phenyl thieno[2,3-b]pyridine,
5-(4-fluorobenzoyl)-3-(N-benzyl-N-methylaminomethyl)-7-(2,6-difluorobenzyl)-4,7-dihydro-4-oxo-2-(4-cyclopropanecarbonylaminophenyl)thieno[2,3-b]pyridine,
3-(N-benzyl-N-methylaminomethyl)-4,7-dihydro-5-isobutyryl-7-(2,6-difluorobenzyl)-2-[4-(3-hydroxy-2-methylpropionylamino)phenyl]-4-oxothieno[2,3-b]pyridine,
3-(N-benzyl-N-methylaminomethyl)-4,7-dihydro-5-isobutyryl-7-(2,6-difluorobenzyl)-2-(4-N'-methoxyureidophenyl)-4-oxothieno[2,3-b]pyridine,
3-(N-benzyl-N-methylaminomethyl)-4,7-dihydro-5-isobutyryl-7-(2,6-difluorobenzyl)-2-[4-[(1-hydroxycyclopropyl)carbonylamino]phenyl]-4-oxothieno[2,3-b]pyridine,
(R)-4,7-dihydro-2-[4-(3-hydroxy-2-methylpropionylamino)phenyl]-7-(2,6-difluorobenzyl)-3-(N-benzyl-N-methylaminomethyl)-5-isobutyryl-4-oxothieno[2,3-b]pyridine,
4,7-dihydro-2-[4-(2-hydroxy-2-methylpropionylamino)phenyl]-7-(2,6-difluorobenzyl)-3-(N-benzyl-N-methylaminomethyl)-5-isobutyryl-4-oxothieno[2,3-b]pyridine,
4,7-dihydro-2-[4-(3-hydroxy-3-methylbutyryl amino)phenyl]-7-(2,6-difluorobenzyl)-3-(N-benzyl-N-methylaminomethyl)-5-isobutyryl-4-oxothieno[2,3-b]pyridine,
(R)-4,7-dihydro-2-[4-(2,3-dihydroxy propionylamino)phenyl-7-(2,6-difluorobenzyl)-3-(N-benzyl-N-methylaminomethyl)-5-isobutyryl-4-oxothieno[2,3-b]pyridine,
3-(N-benzyl-N-methylaminomethyl)-5-benzoyl-7-(2,6-difluorobenzyl)-4,7-dihydro-2-[4-[(1-hydroxycyclopropyl)carbonylamino]phenyl]-4-oxothieno2,3-b]pyridine, and salts thereof.

Compound (I) can be produced in any per se known manner, for example, according to the methods disclosed in WO 95/28405 or analogous methods thereto. Concretely mentioned are the following Production method 1 and Production method 2.

Production method 1:

Compound (I) is produced by reacting compound (II) with a compound of the formula: $R^{1a}COOH$ wherein $R^{1a}$ represents a $C_{1-7}$ alkyl group which may be substituted or a $C_{3-7}$ cycloalkyl group which may be substituted, or a salt thereof or a reactive derivative thereof [hereinafter sometimes referred to briefly as compound (III)].

The "$C_{1-7}$ alkyl group which may be substituted" and the "$C_{3-7}$ cycloalkyl group which may be substituted" for $R^{1a}$ are the same as those mentioned above for the "$C_{1-7}$ alkyl group which may be substituted" and the "$C_{3-7}$ cycloalkyl group which may be substituted" for $R^1$, respectively.

The "reactive derivative" of the "compound of the formula: $R^{1a}COOH$, or a salt thereof or a reactive derivative thereof" includes, for example, a compound of the formula: $R^{1a}Coy$
wherein Y represents halogen and $R^{1a}$ is same as defined above.

The amount of compound (III) to be reacted is about 1 to 3 mol, relative to one mol of compound (II).

This reaction is also carried out in the presence of a base. The "base" is exemplified by inorganic bases such as sodium carbonate, sodium hydrogen carbonate, potassium carbonate, potassium hydrogen carbonate, sodium hydroxide, potassium hydroxide and thallium hydroxide, and organic bases such as triethylamine and pyridine, etc.

The amount of the "base" is about 1 to 10 mol, preferably about 2 to 5 mol, relative to one mol of compound (II).

In the case where a compound of the formula: $R^{1a}COOH$ or a salt thereof is used, a condensing reagent which is generally used in peptide chemistry such as benzotroazol-1-yloxytripyrrolidinophosphonium hexafluorophosphate (PyBop) may be employed to form an amide bond.

This reaction is advantageously carried out in a solvent inert to the reaction. Examples of the solvent include ethers (e.g., ethyl ether, dioxane, dimethoxyethane, tetrahydrofuran, etc.), aromatic hydrocarbons (e.g., benzene, toluene, etc.), amides (e.g., dimethylformamide, dimethylacetamide, etc.), halogenated hydrocarbons (e.g., chloroform, dichloromethane, etc.), and so forth.

The reaction temperature is usually about 0 to 150° C., preferably room temperature (about 15 to 25° C.). The reaction time is usually about 1 to 12 hours.

Compound (II) can be produced in any per se known manner, for example, by the methods disclosed in WO 95/28405 or analogous methods thereto.

Compound (I) wherein $R^1$ is a $C_{1-6}$ alkoxyamino group which may be substituted or a hydroxyamino group which may be substituted can also be produced in according to the method of the following Production method 2.

Production method 2:

Compound (I) is produced by reacting compound (II) with carbonyldiimidazole (N,N'-carbonyldiimidazole; CDI), phosgene (monomer, dimer or trimer) or a chloroformate, followed by reacting with a compound of the formula: $R^{1b}H$ wherein $R^{1b}$ represents a $C_{1-6}$ alkoxyamino group which may be substituted or a hydroxyamino group which may be substituted, or a salt thereof [hereinafter sometimes referred to briefly as compound (IV)].

The "chloroformate" includes, for example, a compound of the formula: Cl-COOY' wherein Y' represents a $C_{1-6}$ alkyl group, such as chloroformate ethyl, etc.

The "$C_{1-6}$ alkoxyamino group which may be substituted" and the "hydroxyamino group which may be substituted" for $R^{1b}$ are the same as those mentioned above for the "$C_{1-6}$ alkoxyamino group which may be substituted" and the "hydroxyamino group which may be substituted" for $R^1$, respectively.

In the reaction of compound (II) with carbonyldiimidazole, phosgene or chloroformates, carbonyldiimidazole, phosgene or chloroformates is used in amount of about 1 to 3 mol, relative to one mol of compound (II).

This reaction is advantageously carried out in a solvent inert to the reaction. Examples of the solvent include ethers (e.g., ethyl ether, dioxane, dimethoxyethane, tetrahydrofuran, etc.), aromatic hydrocarbons (e.g., benzene, toluene, etc.), amides (e.g., dimethylformamide, dimethylacetamide,etc.), halogenated hydrocarbons (e.g., chloroform, dichloromethane, etc.), and so forth.

The reaction temperature is usually about 0 to 150° C., preferably room temperature (about 15 to 25° C.). The reaction time is usually about 1 to 36 hours.

This reaction is also carried out in the presence of a base. The "base" is exemplified by inorganic bases such as sodium carbonate, sodium hydrogen carbonate, potassium carbonate, potassium hydrogen carbonate, sodium hydroxide, potassium hydroxide and thallium hydroxide, and organic bases such as triethylamine and pyridine, etc.

The amount of the "base" is bout 2 to 20 mol, preferably about 5 to 12 mol, relative to one mol of compound (II).

The following reaction with compound (IV) can be carried out in the same condition of the above reaction of compound (II) with carbonyldiimidazole, phosgene or a chloroformate. The amount of compound (IV) is about 2 to 20 mol, preferably about 5 to 10 mol, relative to one mol of compound (II).

The reaction temperature is usually about 0 to 150° C., preferably room temperature (about15 to 25° C.). The reaction time is usually about 1 to 6 hours.

Compound (I) of the present invention may be isolated and purified by ordinary means of separation such as recrystallization, distillation and chromatography, etc. When the compound of the formula (I) is obtained in free form, it can be converted to a salt by per se known methods or analogous thereto. When compound (I) is obtained in salt form, it can be converted to the free form or another salt by per se known methods or analogous thereto.

Salts of compound (I) are preferably physiologically acceptable acid addition salts. Such salts include, for example, salts with inorganic acids (e.g., hydrochloric acid, hydrobromic acid, nitric acid, sulfuric acid, phosphoric acid) and physiologically acceptable acid addition salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid). When compound (I) has an acidic group, it may form a physiologically acceptable salt with an inorganic base (e.g., alkali metals such as sodium, potassium, calcium and magnesium, alkaline earth metals, ammonia) or an organic base (e.g., trimethylamine, triethylamine, pyridine, picoline, ethanolamine, diethanolamine, triethanolamine, dicyclohexylamine, N,N'-dibenzylethylenediamine).

Compound (I) may be a hydrate or a non-hydrate. The hydrate is exemplified by monohydrate, sesquihydrate and dihydrate.

When compound (I) is obtained as a mixture (racemate) of optically active configurations, it can be resolved into the (R)- and (S)-forms by the conventional optical resolution techniques.

Compound (I) of the present invention (hereinafter also referred to as "compound of the present invention") possesses excellent GnRH-antagonizing activity and low toxicity. In addition, it is excellent in oral absorbability, action sustainability, stability and pharmacokinetics. Furthermore, it can be easily produced. The compound of the present invention can therefore be safely used in a mammal (e.g., human, monkey, bovine, horse, dog, cat, rabbit, rat, mouse) for the preventing and/or treating diseases depending on male or female hormones, diseases due to excess of these hormone, etc., by suppressing gonadotropin secretion by its GnRH receptor-antagonizing action to control blood sex hormone concentrations.

For example, the compound of the present invention is useful for preventing and/or treating sex hormone-dependent cancers (e.g., prostatic cancer, uterine cancer, breast cancer, pituitary tumor, etc.), prostatic hypertrophy, hysteromyoma, endometriosis, precocious puberty, amenorrhea, premenstrual syndrome, multilocular ovary syndrome, pimples etc. The compound of the present invention is also useful for the regulation of reproduction in males and females (e.g., pregnancy regulators, menstruation cycle regulators, etc.). The compound of the present invention also be used as a male or female contraceptive, or as a female ovulation inducer. Based on its rebound effect after withdrawal, the compound of the present invention can be used to treat infertility.

In addition, the compound of the present invention is useful for regulation of animal estrous, improvement of meat quality and promotion of animal growth in the field of animal husbandry. The compound of the present invention is also useful as a fish spawning promoter.

Although the compound of the present invention can be used alone, it is effective to use in combination with a steroidal or non-steroidal anti-androgen agent or anti-estrogen agent. The compound of the present invention can also be used to suppress the transient rise in blood testosterone concentration (flare phenomenon) observed in administration of a super-agonist such as Leuprorelin acetate. The compound of the present invention can be used in combination with a super-agonist such as leuprorelin acetate, gonadrelin, buserelin, triptorelin, goserelin, nafarelin, histrelin, deslorelin, meterelin, lecirelin, and so forth. Among others, preferred is leuprorelin acetate. The compound of the present invention also may be used with a chemotherapeutic agent for cancer. A preferred example of such combination is the compound of the present invention in combination with chemotherapeutic agents such as ifosfamide, UTF, adriamycin, peplomycin and cisplatin for prostatic cancer. For breast cancer, the compound of the present invention can be used with chemotherapeutic agents such as cyclophosphamide, 5-FU, UFT, methotrexate, adriamycin, mitomycin C and mitoxantrone.

When the compound of the present invention is used for preventing and/or treating (as a prophylactic and/or therapeutic agent for) the above-mentioned diseases or used in the filed of animal husbandry or fishery, it can be administered orally or non-orally, as formulated with a pharmaceutically acceptable carrier, normally in the form of solid preparations such as tablets, capsules, granules and powders for oral administration, or in the form of intravenous, subcutaneous, intramuscular or other injections, suppositories or sublingual tablets for non-oral administration. It may also be sublingually, subcutaneously, intramuscularly or otherwise administered in the form of sustained-release preparations of sublingual tablets, microcapsules etc. Depending on symptom severity; subject age, sex, weight and sensitivity; duration and intervals of administration; property, dispensing and kind of pharmaceutical preparation; kind of active ingredient etc., daily dose is not subject to limitation. For use in the treatment of the above-described sex hormone-dependent cancers (e.g., prostatic cancer, uterine cancer, breast cancer, pituitary tumor), prostatic hypertrophy, hysteromyoma, endometriosis, precocious puberty etc., daily dose is normally about 0.01 to 30 mg, preferably about 0.02 to 10 mg, and more preferably 0.1 to 10 mg, per kg weight of mammal, normally in 1 to 4 divided dosages.

The above doses are applicable to the use of the compound of the present invention in the filed of animal husbandry or fishery. Daily dose is about 0.01 to 30 mg, preferably about 0.1 to 10 mg, per kg weight of subject organism, normally in 1 to 3 divided dosages.

In the pharmaceutical composition of the present invention, the amount of compound (I) is 0.01 to 100% by weight or so of the total weight of the composition.

Pharmaceutically acceptable carriers are various organic or inorganic carrier substances in common use as pharmaceutical materials, including excipients, lubricants, binders and disintegrants for solid preparations, and solvents, dissolution aids, suspending agents, isotonizing agents, buffers and soothing agents for liquid preparations. Other pharmaceutical additives such as preservatives, antioxidants, coloring agents and sweetening agents may be used as necessary.

Preferable excipients include, for example, lactose, sucrose, D-mannitol, starch, crystalline cellulose and light silicic anhydride. Preferable lubricants include, for example, magnesium stearate, calcium stearate, talc and colloidal silica. Preferable binders include, for example, crystalline cellulose, sucrose, D-mannitol, dextrin, hydroxypropyl cellulose, hydroxypropylmethyl cellulose and polyvinylpyrrolidone. Preferable disintegrants include, for example, starch, carboxymethyl cellulose, carboxymethyl cellulose calcium, crosslinked carmellose sodium and carboxymethyl starch sodium. Preferable solvents include, for example, water for injection, alcohol, propylene glycol, macrogol, sesame oil and corn oil. Preferable dissolution aids include, for example, polyethylene glycol, propylene glycol, D-mannitol, benzyl benzoate, ethanol, trisaminomethane, cholesterol, triethanolamine, sodium carbonate and sodium citrate. Preferable suspending agents include, for example, surfactants such as stearyltriethanolamine, sodium lauryl sulfate, laurylaminopropionic acid, lecithin, benzalkonium chloride, benzethonium chloride and monostearic glycerol: and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include, for example, sodium chloride, glycerol and D-mannitol. Preferable buffers include, for example, buffer solutions of phosphates, acetates, carbonates, citrates etc. Preferable soothing agents include, for example, benzyl alcohol. Preferable preservatives include, for example, paraoxybenzoic acid esters, chlorobutanol, benzyl alcohol, phenethyl alcohol, dehydroacetic acid and sorbic acid. Preferable antioxidants include, for example, sulfites and ascorbic acid.

By adding suspending agents, dissolution aids, stabilizers, isotonizing agents, preservatives, and so forth, the compound of the present invention can be prepared as an intravenous, subcutaneous or intramuscular injection by a commonly known method. In such cases, the compound of the present invention can be freeze-dried as necessary by a commonly known method. In administration to humans, for example, the compound of the present invention can be safely administered orally or non-orally as such or as a pharmaceutical composition prepared by mixing it with a pharmacologically acceptable carrier, excipient and diluent selected as appropriate.

Such pharmaceutical compositions include oral preparations (e.g., powders, granules, capsules, tablets), injections, drip infusions, external preparations (e.g., nasal preparations, transdermal preparations) and suppositories (e.g., rectal suppositories, vaginal suppositories).

These preparations can be produced by commonly known methods in common use for pharmaceutical making processes.

An injection can be produced by, for example, preparing the compound of the present invention as an aqueous injection along with a dispersing agent (e.g., Tween 80, produced by Atlas Powder Company, USA, HCO 60, produced by Nikko Chemicals Co., Ltd., polyethylene glycol, carboxymethyl cellulose, sodium alginate), a preservative (e.g., methyl paraben, propyl paraben, benzyl alcohol), an isotonizing agent (e.g., sodium chloride, mannitol, sorbitol, glucose) and other additives, or as an oily injection in solution, suspension or emulsion in a vegetable oil such as olive oil, sesame oil, cottonseed oil or corn oil, propylene glycol or the like.

An oral preparation can be produced by shaping the compound of the present invention by a commonly known method after addition of an excipient (e.g., lactose, sucrose, starch), a disintegrant (e.g., starch, calcium carbonate), a binder (e.g., starch, gum arabic, carboxymethyl cellulose, polyvinylpyrrolidone, hydroxypropyl cellulose), a lubricant (e.g., talc, magnesium stearate, polyethylene glycol 6000) and other additives, and, where necessary, coating the shaped product for the purpose of taste masking, enteric dissolution or sustained release by a commonly known method. Coating agents for this purpose include, for example, hydroxypropylmethyl cellulose, ethyl cellulose, hydroxymethyl cellulose, hydroxypropyl cellulose, polyoxyethylene glycol, Tween 80, Prulonic F68, cellulose acetate phthalate, hydroxypropylmethyl cellulose phthalate, hydroxymethyl cellulose acetate succinate, Eudragit (produced by Rohm Company, Germany; methacrylic acid/ acrylic acid copolymer) and dyes (e.g., iron oxide, titanium dioxide). For an enteric preparation, an intermediate phase may be provided between the enteric phase and the drug-containing phase for the purpose of separation of the two phases by a commonly known method.

An external preparation can be produced by compounding the compound of the present invention as a solid, semi-solid or liquid composition by a commonly known method. Such a solid composition is produced by, for example, powdering the compound of the present invention as such or in mixture with an excipient (e.g., glycol, mannitol, starch, microcrystalline cellulose), a thickening agent (e.g., natural rubber, cellulose derivative, acrylic acid polymer) and other additives. Such a liquid composition is produced by preparing the compound of the present invention as an oily or aqueous suspension in almost the same manner as with the injection. The semi-solid composition is preferably an aqueous or oily gel, or an ointment. All these compositions may contain pH regulators (e.g., carbonic acid, phosphoric acid, citric acid, hydrochloric acid, sodium hydroxide), preservatives (e.g., paraoxybenzoic acid esters, chlorobutanol, benzalkonium chloride) and other additives.

A suppository is produced by preparing the compound of the present invention as an oily or aqueous solid, semi-solid or liquid composition by a commonly known method. Useful oily bases for such compositions include glycerides of higher fatty acids (e.g., cacao fat, uitepsols, produced by Dynamite Nobel Company, Germany), moderate fatty acids (e.g., MIGLYOL, produced by Dynamite Nobel Company, Germany), and vegetable oils (e.g., sesame oil, soybean oil, cottonseed oil). Aqueous bases include, for example, polyethylene glycols and propylene glycol. Bases for aqueous gels include, for example, natural rubbers, cellulose derivatives, vinyl polymers and acrylic acid polymers.

BEST MODE FOR CARRYING OUT THE INVENTION

The present invention is hereinafter described in more detail by means of, but is not limited to, the following reference examples, examples, preparation examples and experimental examples.

$^1$H-NMR spectra are determined with tetramethylsilane as the internal standard, using the GEMINI 200 (200 MHz) spectrometer (produced by Varian, Ltd.), the LAMBDA 300 (300 MHz) spectrometer (produced by JEOL, Ltd.) or the Bruker AM500 (500 MHz) spectrometer (produced by Bruker); all δ values are shown in ppm. Unless otherwise specifically indicated, "%" is by weight. Yield indicates mol/mol %.

The symbols used herein have the following definitions:
s: singlet
d: doublet
t: triplet
dt: double triplet
m: multiplet
br: broad The term "at room temperature" indicates the range from about 15 to 25° C., but is not to be construed as strictly limitative.

EXAMPLES

Reference Example 1

Production of 2-amino-5-phenylthiophen-3-carboxylic acid ethyl ester

To a mixture of ethyl cyanoacetate (6.1 g, 50 mmol), sulfur (1.61 g, 50 mmol), triethylamine (3.5 ml, 25 mmol), and dimethylformamide (10 ml), phenylacetaldehyde (50% solution in diethyl phthalate; 12.05 g, 50 mmol) was added dropwise with stirring at 45° C. over 20 minutes. After stirring at 45° C. for 9 hours, the reaction mixture was concentrated and the obtained residue was extracted with ethyl acetate, washed with saline and dried (MgSO$_4$), the solvent was distilled off under reduced pressure. The residue was chromatographed on silica gel and recrystallized from ether-hexane to yield pale yellow tabular crystals (5.55 g, 45%).

mp 124.5–125.5° C. (lit.; 123–124° C.). Elemental analysis for C$_{1-3}$H$_{1-3}$NO$_2$S; C (%) H (%) N(%), Calculated 63.13; 5.30; 5.66; Found: 62.99; 5.05; 5.63; $^1$H-NMR (300 MHz, CDCl$_3$) δ: 1.37 (3H, t, J=7.1 Hz), 4.30 (2H, d, J=7.1 Hz), 5.97 (2H, br), 7.17–7.46 (6H, m). IR (KBr): 3448, 3320, 1667, 1590, 1549 cm$^{-1}$.

Reference Example 2

Production of 2-amino-4-methyl-5-(4-methoxyphenyl)thiophen-3-carboxylic acid ethyl ester A mixture of 4-methoxyphenylacetone (16.5 g, 0.10 mol), ethyl cyanoacetate (12.2 g, 0.10 mol), ammonium acetate (1.55 g, 20 mmol), acetic acid (4.6 ml, 80 mmol), and benzene (20 ml) was heated and refluxed for 24 hours, while the water being produced was removed using a Dean-Stark apparatus. After cooling, the reaction mixture was concentrated under reduced pressure and the residue was partitioned between dichloromethane and aqueous sodium bicarbonate. After the organic layer was washed with saline and dried (MgSO$_4$), the solvent was distilled off under reduced pressure. To a solution in ethanol (30 ml) of the obtained residue, were added sulfur (3.21 g, 0.10 mol) and diethylamine (10.4 ml, 0.10 mol), followed by stirring at 50 to 60° C. for 2 hours, successively the reaction mixture was concentrated. The obtained residue was extracted with ethyl acetate, washed with saline and dried (MgSO$_4$), the solvent was distilled off under reduced pressure. The residue was chromatographed on silica gel and recrystallized from ether-hexane to yield light yellow tabular crystals (11.5 g. 40%).

mp 79–80° C. Elemental analysis for C$_{15}$H$_{17}$NO$_3$S; C(%), H(%), N(%), S(%), Calculated 61.83; 5.88; 4.81; 11.01; Found: 61.81; 5.75; 4.74; 10.82; $^1$H-NMR (200 MHz, CDCl$_3$) δ: 1.37 (3H, t, J=7.1 Hz), 2.28(3H, s), 3.83 (3H, s), 4.31 (2H, q, J=7.1 Hz), 6.05 (2H, brs), 6.91 (2H, d, J=8.8 Hz), 7.27 (2H, d, J=8.8 Hz). IR (KBr): 3426, 3328, 1651, 1586, 1550, 1505, 1485 cm$^{-1}$. FAB-MS m/z: 291 (M$^+$).

Reference Example 3

Using some acetone derivatives in place of 4-methoxyphenylacetone, the following compound was obtained in the same manner as in Reference Example 2.

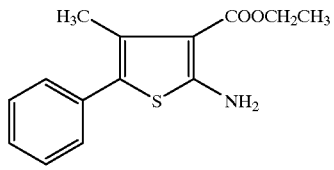

Yield: 40% mp 64–65° C.

Reference Example 4

Production of [3-ethoxycarbonyl-5-(4-methoxyphenyl)-4-methylthiophen-2-yl] aminomethylenemalonic acid diethyl ester To the compound obtained in Reference Example 2 (10 g, 34.3 mmol), ethoxymethylenemalonic acid diethyl ester (7.45 g, 34.5 mmol) was added, followed by stirring at 120° C. for 2 hours. After the reaction mixture was cooled, the crystal precipitated was collected by filtration via the addition of ether, again washed with ether, and dried over phosphorus pentaoxide under reduced pressure to yield yellow crystals (14.2 g, 90%).

mp 122–123° C. $^1$H-NMR (200 MHz, CDCl$_3$) δ: 1.32 (3H, t, J=7.1 Hz), 1.38 (3H, t, J=7.2 Hz), 1.41 (3H, t, J=7.2 Hz), 2.34 (3H, s), 3.85 (3H, s), 4.25 (2H, q, J=7.1 Hz), 4.38 (2H, q, J=7.2 Hz), 4.45 (2H, q, J=7.2 Hz), 6.95 (2H, d, J=8.8 Hz), 7.31 (2H, d, J=8.8 Hz), 8.22 (1H, d, J=13.4 Hz), 12.74 (1H, d, J=13.1 Hz). IR (KBr): 2984, 1720, 1707, 1688, 1653, 1599, 1518, 1499 cm$^{-1}$.

Reference Example 5

Using the compound obtained in Reference Example 3 as a starting material, the following compound was obtained in the same manner as in Reference Example 4.

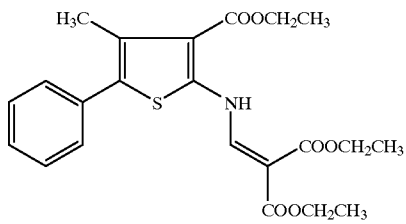

Yield: 92% mp 108–109° C.

Reference Example 6

Production of 3-carboxy-5-[(4-methoxyphenyl)-4-methylthiophen-2-yl]aminomethylenemalonic acid diethyl ester To a solution in dioxane (20 ml) of the compound obtained in Reference Example 4 (7.0 g, 15.2 mmol) was added, a solution of potassium hydroxide (5.0 g, 75.7 mmol) in ethanol (30 ml) with stirring at 60 to 70° C. After stirring at this temperature for 1 hour, the reaction mixture was kept standing at room temperature for 1 hour. To the mixture was added 2 N hydrochloric acid (40 ml, 80 mmol) with ice cooling, the reaction mixture was concentrated under reduced pressure. The yellow precipitate was collected by filtration, washed with cold water-ethanol, and dried over phosphorus pentaoxide under reduced pressure to yield yellow powders (6.1 g, 93%).

mp 184–187° C. $^1$H-NMR (200 MHz, DMSO-d$_6$) δ: 1.24 (3H, t, J=7.1 Hz), 1.28 (3H, t, J=7.2 Hz), 2.30 (3H, s), 3.80 (3H, s), 4.15 (2H, q, J=7.1 Hz), 4.24 (2H, q, J=7.2 Hz), 7.03 (2H, d, J=8.7 Hz), 7.37 (2H, d, J=8.7 Hz), 8.08 (1H, d, J=13.6 Hz), 12.41 (1H, d, J=13.6 Hz). IR (KBr): 3422, 2980, 1719, 1653, 1607, 1551, 1512 cm$^{-1}$.

Reference Example 7

Using the compound obtained in Reference Example 5 as a starting material, the following compound was obtained in the same manner as in Reference Example 6.

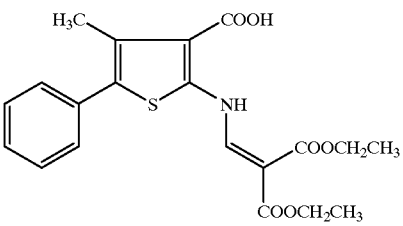

Yield: 98% mp 187–190° C.

Reference Example 8

Production of 4-hydroxy-2-(4-methoxyphenyl)-3-methylthieno[2,3-b]pyridine-5-carboxylic acid ethyl ester With stirring at 120° C. small portions of the compound obtained in Reference Example 6 (6.0 g, 13.8 mmol) was added to polyphoshoric acid ester (PPE) (90 ml). After stirring at the same temperature for 30 minutes, the reaction mixture was poured into ice water and extracted with ethyl acetate. The combined extracts were washed with saline, and dried (MgSO$_4$), the solvent was distilled off under reduced pressure. The obtained residue was chromatographed on silicageltoyieldyellowpowders (3.65 g, 77%). For a sample for elemental analysis, the powders obtained were recrystallized from ethanol to yield yellow crystals.

mp 162–163 ° C. Elemental analysis for C$_{18}$H$_{17}$NO$_4$S; C(%), H(%), N(%) S(%), Calculated : 62.96; 4.99; 4.08; 9.34; Found: 62.89; 5.04; 4.01; 9.34; $^1$H-NMR (200 MHz, CDCl$_3$) δ: 1.47 (3H, t, J=7.1 Hz), 2.63 (3H, s), 4.87 (3H, s), 4.49 (2H,q, J=7.1 Hz), 6.99 (2H, d. J=8.8 Hz), 7.44 (2H, d, J=8.8 Hz), 8.84 (1H,s), 12.11 (1H, s). IR (KBr): 3434, 2992, 1692, 1601, 1582, 1535, 1504 cm$^{-1}$. FAB-MS m/z: 344 (M$^+$).

Reference Example 9

Using the compound obtained in Reference Example 7 as a starting material, the following compound was obtained in the same manner as in Reference Example 8.

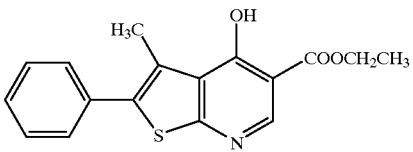

Yield: 60% mp 155–157° C.

Reference Example 10

Production of 4-hydroxy-2-(4-nitrophenyl)-3-methylthieno[2,3-b]pyridine-5-carboxylic acid ethyl ester To a solution in concentrated sulfuric acid (10 ml) of the compound obtained in Reference Example 9 (3.76 g, 12.0 mmol) was added dropwise a solution of sodium nitrate (1.27 g, 15.0 mmol) in concentrated sulfuric acid (5 ml) with ice cooling. After stirring at this temperature for 30 minutes, the reaction mixture was poured into ice water and extracted with chloroform. The combined extracts were washed with saline, and dried (MgSO$_4$), the solvent was distilled off under reduced pressure. The obtained residue was chromatographed on silica gel to yield yellow powders, which was recrystallized from ethanol to yield yellow crystals (1.75 g, 41%).

mp 260–261° C. Elemental analysis for $C_{17}H_{14}N_2O_5S$; C(%), H(%), N(%), Calculated 56.98; 3.94; 7.82; Found: 56.66; 3.91; 7.86; $^1$H-NMR (200 MHz, CDCl$_3$) δ: 1.49(3H, t, J=7.1 Hz), 2.70(3H, s), 4.51 (2H, q, J=7.1 Hz), 7.70(2H, d, J=8.8 Hz), 8.34(2H, d, J=8.8 Hz), 8.89(1H,s), 12.27(1H, s). IR (KBr): 3002, 1692, 1605, 1514, 1350, 1290 cm$^{-1}$. FAB-MS m/z: 358 (M$^+$).

Reference Example 11

Production of 4,7-dihydro-7-(2-methoxybenzyl)-2-(4-methoxyphenyl)-3-methyl-4-oxothieno[2,3-b]pyridine-5-carboxylic acid ethyl ester To a suspension of sodium hydride (60% dispersion in oil; 123 mg, 3.08 mmol) in dimethylformamide (3 ml) was added a solution of the compound obtained in Reference Example 8 (1.0 g, 2.91 mol) in dimethylformamide (20 ml) under nitrogen stream with ice cooling. After stirring at this temperature for 30 minutes, to the mixture was added dropwise a solution of 2-methoxybenzyl chloride (0.92 g, 5.87 mmol) in dimethylformamide (3 ml). After stirring at room temperature for 23 hours and at 70 ° C. for 2 hours, the reaction mixture was concentrated, and then the obtained residue was partitioned between ethyl acetate and an aqueous solution of ammonium chloride. The water layer was extracted with ethyl acetate. The combined extracts were washed with saline, and dried (MgSO$_4$), the solvent was distilled off under reduced pressure. The obtained residue was chromatographed on silica gel to yield light yellow amorphous powders (0.95 g, 70%). For a sample for elemental analysis, the obtained powders were recrystallized from dichloromethane-ether to yield yellow prismatic crystals.

mp 165–167° C. Elemental analysis for $C_{26}H_{25}NO_5S$ 0.5H$_2$O; C(%), H(%), N(%), Calculated: 66.08; 5.55; 2.96; Found: 66.33; 5.44; 2.74; $^1$H-NMR (200 MHz, CDCl$_3$) δ: 1.41(3H, t, J=7.1 Hz), 2.65(3H, s), 3.85(3H, s), 3.86(3H, s), 4.39(2H, q, J=7.1 Hz), 5.16(2H, s), 6.92–7.00(4H, m), 7.21–7.41(4H, m), 8.41(1H, s). IR (KBr): 2980, 1727, 1684, 1609, 1590, 1497, 1464 cm$^{-1}$.

Reference Example 12

The following compound was produced by the same method as described in, Reference Example 11, using benzyl 2,6-difluoro chloride in place of 2-methoxybenzyl chloride with the compound obtained in Reference Example 10 as the starting material.

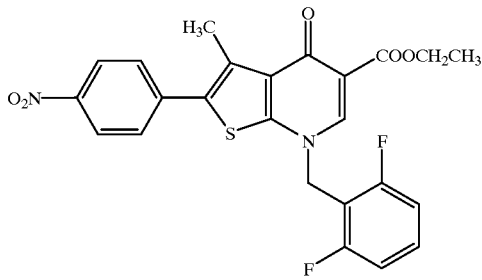

Yield: 81% mp 215–217° C.

Reference Example 13

Production of 3-bromomethyl-4,7-dihydro-7-(2-(methoxybenzyl)-2-(4-methoxyphenyl)-4-oxothieno[2,3-b]pyridine-5-carboxylic acid ethyl ester A mixture of the compound obtained in Reference Example 11 (0.35 g, 0.755 mmol), N-bromosuccinimide (0.135 g, 0.758 mmol), α,α'-azobisisobutyronitrile (13 mg, 0.079 mmol), and carbon tetrachloride (5 ml) was heated and refluxed for 2 hours. After cooling, the insoluble substances were filtered off, and then the filtrate was diluted with chloroform. After the organic layer was washed with saline and dried (MgSO$_4$), the solvent was distilled off under reduced pressure. The obtained residue was recrystallized from ethyl acetate to yield colorless needles (0.272 g, 66%).

mp 200–201° C. Elemental analysis for $C_{26}H_{24}NO_5SBr$; C(%), H(%), N(%), Calculated: 57.57; 4.46; 2.58; Found: 57.75; 4.31; 2.31; $^1$H-NMR (200 MHz, CDCl$_3$) δ: 1.40(3H, t, J=7.1 Hz), 3.86(6H, s), 4.40(2H,q, J=7.1 Hz), 5.05(2H,s), 5.16(2H, s), 6.92–7.04(4H, m), 7.23–7.28(1H,m), 7.34–7.43 (1H,m), 7.57(2H, d, J=8.9 Hz), 8.46(1H, s). IR (KBr): 2980, 1725, 1607, 1588, 1497 cm$^{-1}$.

Reference Example 14

Using the compounds obtained in Reference Examples 12, 22 and 27 as a starting material, respectively, the following compounds (Reference Examples 14-1 to 14-3) were obtained in the same manner as in Reference Example 13.

Reference Example 14-1:

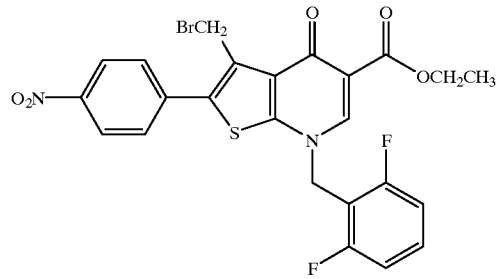

Yield: 81% mp 200–202 ° C.

Reference Example 14-2:

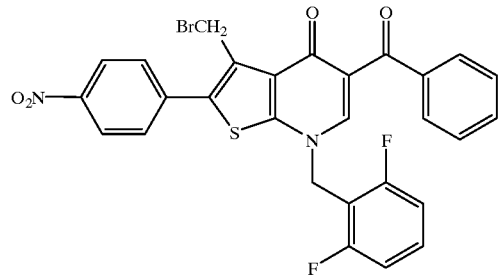

Yield: 80% Amorphous.

Reference Example 14-3:

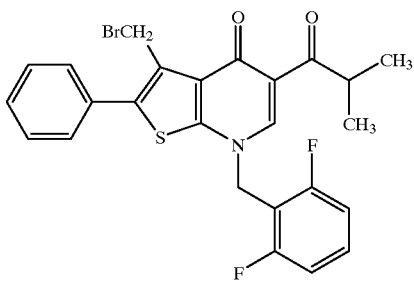

Yield: 79% mp 189–192° C.

Reference Example 15

Production of 3-benzylaminomethyl-4,7-dihydro-7-(2-methoxybenzyl)-2-(4-methoxyphenyl)-4-oxothieno[2,3-b]pyridine-5-carboxylic acid ethyl ester hydrochloride To a solution of the compound obtained in Reference Example 13 (0.245 g, 0.452 mmol) in dimethylformamide (5 ml) were added triethylamine (0.10 ml, 0.717 mmol) and benzylamine (80 μl, 0.732 mmol) with ice cooling. After stirring at room temperature for 1.5 hours, the reaction mixture was concentrated, and then the obtained residue was partitioned between ethyl acetate and saturated aqueous sodium bicarbonate. The water layer was extracted with ethyl acetate. The combined organic extracts were dried (MgSo$_4$), the solvent was distilled off under reduced pressure. The obtained residue was chromatographed on silica gel to yield a colorless oil (0.135 g, 53%). To a solution of this oil in ethanol (4 ml) was added 10 N ethanolic hydrochloric acid (0.2 ml) with ice cooling, followed by stirring at this temperature for 10 minutes. The reaction mixture was concentrated, and then the obtained residue was crystallized from ethyl acetate-ether to yield the hydrochloride (0.113 g) as white crystals.

mp [Hydrochloride] 118–119° C. Elemental analysis for $C_{33}H_{32}N_2O_5S$ HCl 0.9H$_2$O; C(%), H(%), N(%), Calculated: 63.79; 5.64; 4.51; Found: 64.03; 5.44; 4.51; $^1$H-NMR (300 MHz, CDCl$_3$) [Free amine] δ: 1.40(3H, t, J=7.1 Hz), 2.05 (1H, br),3.81(3H, s), 3.86(3H, s), 3.87(2H, s), 3.94(2H, s), 4.40(2H. q, J=7.1 Hz), 5.18(2H, s), 6.80(2H, d, J=8.8 Hz), 6.91–6.99(2H, m), 7.20–7.42(9H, m), 8.45(1H, s). IR (KBr) [Hydrochloride]: 3422, 2938, 1719, 1605, 1560, 1545, 1502, 1460 cm$^{-1}$.

Reference Example 16

Production of 4-methyl-2-[(4-methyl-3-oxo-1-penten-1-yl)amino]-5-phenylthiophen-3-carboxylic acid ethyl ester The compound obtained in Reference Example 3 (10 g), 1-methoxy-4-methyl-1-penten-3-one of 85% content (6.9 g), p-toluenesulfonic acid monohydrate (0.219 g), and toluene (100 ml) were mixed and stirred at room temperature for 2.5 hours. After the reaction mixture was diluted with ethyl acetate and washed with a saturated aqueous solution of sodium hydrogen carbonate, the water layer was extracted with ethyl acetate. The combined extracts were washed with saturated saline, the organic layers were dried over anhydrous magnesium sulfate. The residue was crystallized via the addition of a seed crystal, after which it was triturated with hexane, collected by filtration, and washed, to yield the title compound (12.64 g, 92%). mp 104–108° C.

Reference Example 17

Production of 4,7-dihydro-7-(2-methoxybenzyl)-2-(4-methoxyphenyl)-3-methyl-4-oxothieno[2,3-b]pyridine-N-benzyl piperazinyl-5-carboxamide To 1-benzylpiperazine (0.77 g, 4.37 mmol) was added dropwise a solution of diisobutyl aluminum hydride (DIBAL) in toluene (1.5 N, 2.9 ml, 4.37 mmol) with ice cooling. After the addition was completed, the solution was allowed to warm to room temperature and stirred for further 0.5 hours. To this solution was added a solution of the compound obtained in Reference Example 11 (0.50 g, 1.08 mmol) in toluene (5 ml) at room temperature. After the mixture was further stirred at room temperature for 15 hours. methylene chloride (30 ml) was added. After water washing, the solution was dried over sodium sulfate, and then the solvent was concentrated under reduced pressure to yield a solid (1.03 g), which was recrystallized from methylene chloride-n-hexane to yield the title compound (0.48 g, 78%).

mp 233–235° C. Elemental analysis for $C_{35}H_{35}N_3O_4S$ 1/2H$_2$O; C(%), H(%), N(%), S(%), Calculated: 69.75; 6.02; 6.97; 5.32; Found: 69.88; 6.06; 6.98; 5.39; $^1$H-NMR (300 MHz, CDCl$_3$) δ: 2.45–2.55(4H, m), 2.63(3H, s), 3.43–3.49 (2H,m), 3.55(2H, s), 3.73–3.82(2H,m), 3.84(6H, s), 5.11 (2H, s), 6.89–6.98(4H,m), 7.21–7.40(9H,m), 7.79(1H, s).

Reference Example 18

Using the compound obtained in Reference Example 12 as a starting material and N.0-dimethylhydroxy in place of 1-benzylpiperazine, the following compound was obtained in the same manner as in Reference Example 17.

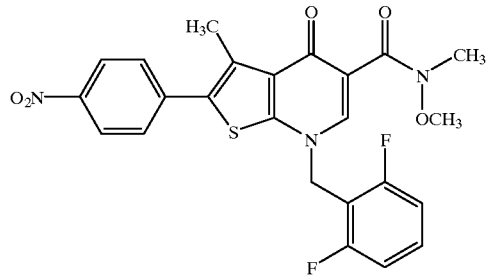

Yield: 80% mp 223–224° C.

Reference Example 19

Production of 4-hydroxy-5-isobutyryl-3-methyl-2-phenylthieno[2,3-b]pyridine

The compound obtained in Reference Example 16 (50 g) and diphenyl ether (500 ml) were mixed, and then this mixture was heated and refluxed for 4 hours, while the ethanol being produced with the progress of the reaction was distilled off. After cooling, the diphenyl ether was distilled off under reduced pressure, and then the crude crystal precipitated was washed with n-hexane to yield the title compound (35.1 g, 81%). mp 114–117° C.

Reference Example 20

Using the compound obtained in Reference Example 14-1 as starting material and N-methylbenzylamine in place of benzylamine, the following compounds (Reference Examples 20-1 to 20-3) were obtained in the same manner as in Reference Example 15.

Reference Example 20-1:

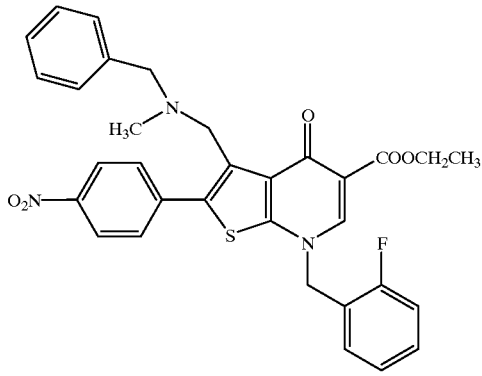

Yield: 83% mp 140–144° C.

Reference Example 20-2:

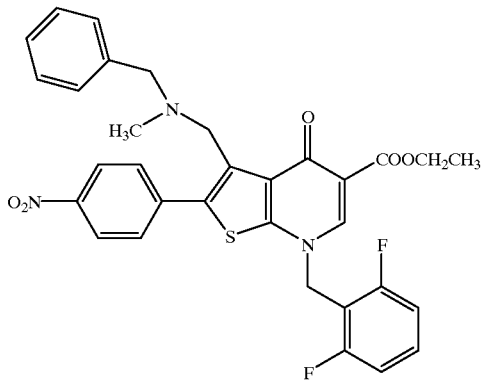

Yield: 91% mp 145–147° C.

Reference Example 20-3:

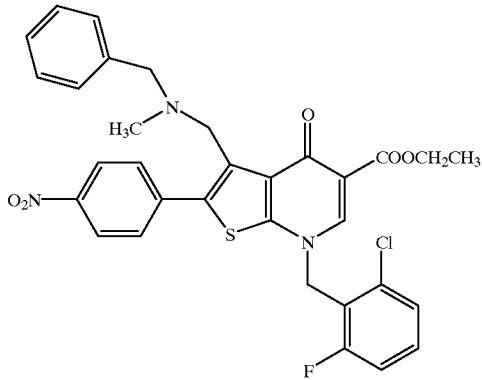

Yield: 78% mp 175–177° C.

Reference Example 21

Using the compounds obtained in Reference Example 20 as starting materials, the following compounds (Reference Examples 21-1 to 21-3) were obtained in the same manner as in Reference Example 28.

Reference Example 21-1:

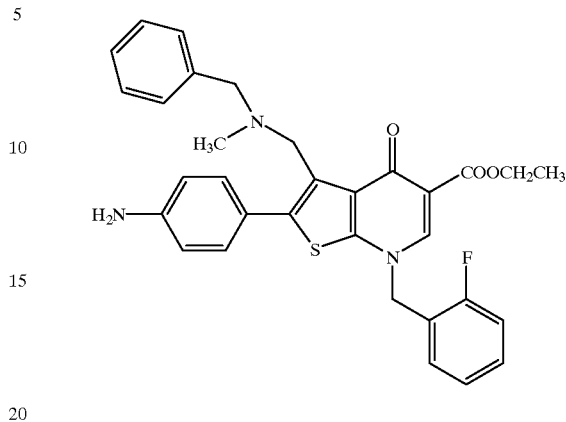

Yield: 79% mp 158–160° C.

Reference Example 21-2:

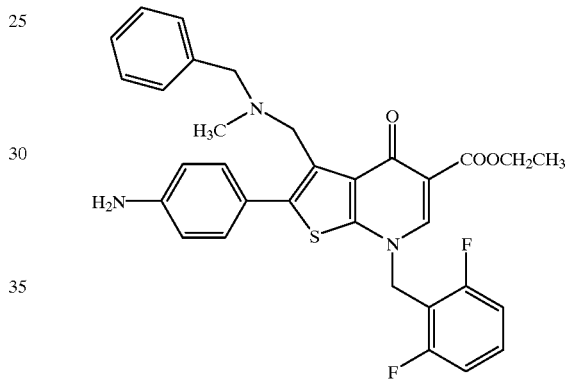

Yield: 96% mp 195–196° C.

Reference Example 21-3:

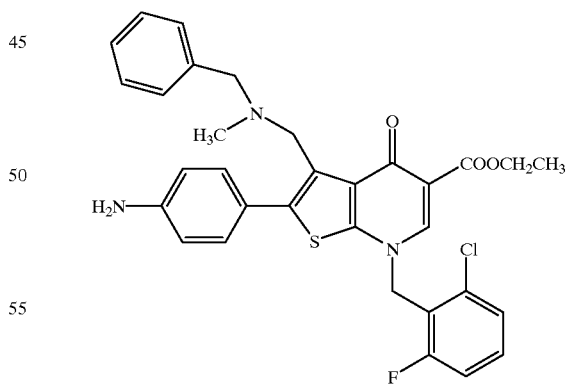

Yield: 71% mp 144–146° C.

Reference Example 22

Production of 7-(2,6-difluorobenzyl)-4,7-dihydro-5-isobutyryl-3-methyl-4-oxo-2-phenyl-thieno[2,3-b]pyridine The compound obtained in Reference Example 19 (35 g), potassium carbonate (18.6 g), and N,N-dimethylformamide (280 ml) were mixed, and then 2,6-difluorobenzyl bromide (27.9 g) was added, followed by stirring at room temperature for 4 hours. To the reaction mixture was added dropwise water (560 ml), followed by stirring for 30 minutes, and then the mixture was stirred for 1 hour with ice cooling. The crude crystal was collected by filtration, washed with water, and dried, successively suspended in a 1:1 mixed solvent (250 ml) of ethyl acetate and diisopropyl ether and stirred at 25 to 40° C. for 1 hour, then stirred with ice cooling for 1 hour, the residual crystal was collected by filtration and washed with the above mixed solvent (125 ml) to yield the title compound (44.6 g, 92%).

mp 205–207° C.

Reference Example 23

Using the compounds obtained in Reference Example 14-2 and Reference Example 24 as starting materials and N-methylbenzylamine in place of benzylamine, the following compounds (Reference Examples 23-1 to 23-2) were obtained in the same manner as in Reference Example 15.

Reference Example 23-1:

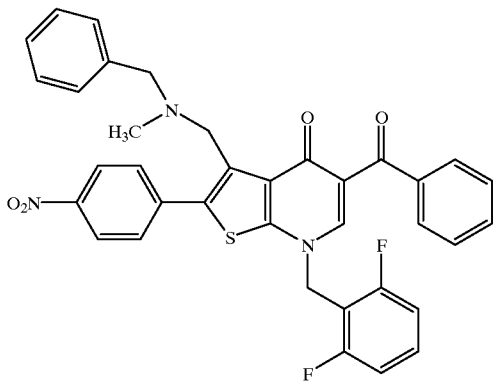

Yield: 83% mp 197–199° C.

Reference Example 23-2:

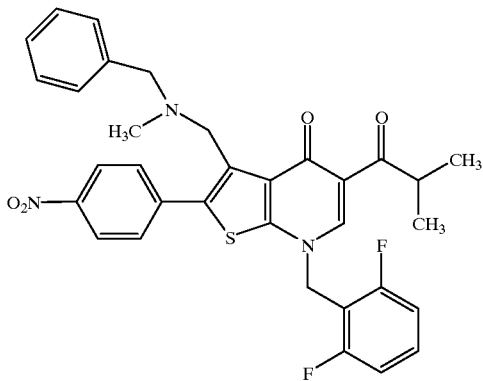

Yield: 66% mp 151–152° C.

Reference Example 24

Production of 3-bromomethyl-7-(2,6-difluorobenzyl)-4,7-dihydro-5-isobutyryl-2-(4-nitrophenyl)- 4-oxothieno[2,3-b]pyridine After the compound obtained in Reference Example 14-3 (1 g) was dissolved in methanesulfonic acid (5 ml) with cooling at 10 to 12° C., a solution of sodium nitrate (0.165 g) in methanesulfonic acid (2.5 ml) was added dropwise to this mixture. After being stirred as was for 2 hours, the mixture was poured into cold water, and then the crystal precipitated was collected by filtration, washed with water and diisopropyl ether, and dried to yield a crude product (1.04 g), which was then triturated with ethyl acetate (15 ml), then cooled with ice, filtered, and washed with cold ethyl acetate to yield the title compound (0.647 g, 59.5%). mp 202 to 204° C. (recrystallized from methanol).

Reference Example 25

Production of 4,7-dihydro-7-(2,6-difluorobenzyl)-2-(4-nitrophenyl)-3-(N-benzyl-N-methylaminomethyl)-4-oxothieno[2,3-b]pyridine-5-(N-isopropyl)carboxamide To a solution of isopropylamine (0.296 g, 5 mmol) in anhydrous methylene chloride (5 ml) was added dropwise a solution of trimethyl aluminum in hexane (15%, 2.41 ml, 5.0 mmol) at, 0° C. After the addition was completed, the solution was allowed to warm to room temperature and further stirred for 1 hour. To this solution was added a solution of the compound obtained in Reference Example 20-2 (0.12 g, 0.25 mmol) in anhydrous methylene chloride (3 ml) with ice cooling (0° C.) over 30 minutes. After the mixture was stirred at room temperature for further 1 hour, chloroform (50 ml) was added, followed by washing with water. The combined organic layers were dried with sodium sulfate, and then the solvent was concentrated under reduced pressure to yield a solid, which was recrystallized from chloroformethyl acetate-ethyl ether to yield colorless crystals (0.096 g, 70%). mp 200–202° C.

$^1$H-NMR (500 MHz, CDCl$_3$)[Free amine]δ: 1.30(6H, d, J=6.7 Hz), 2.15(3H, s), 3.66(2H, s), 4.18(2H, s), 4.18–4.31 (1H, m), 5.32(2H, s), 7.00(2H, t, J=7.26 Hz), 7.13–7.25(5H, m), 7.42(1H, t, J=7.3 Hz), 8.02(2H, d, J=8.9 Hz), 8.26(2H, d, J=8.9 Hz), 8.73(1H, s), 10.02(1H, d, J=9.1 Hz). IR (KBr): 2974, 1661, 1597, 1547, 1497, 1346, 1212, 1035 cm$^{-1}$ FAB-Mass m/z 617(MH)$^+$ Reference Example 26

Using the compound obtained in Reference Example 20-2 as a starting material and N,O-dimethylhydroxyamine, the following compound was obtained in the same manner as in Reference Example 25.

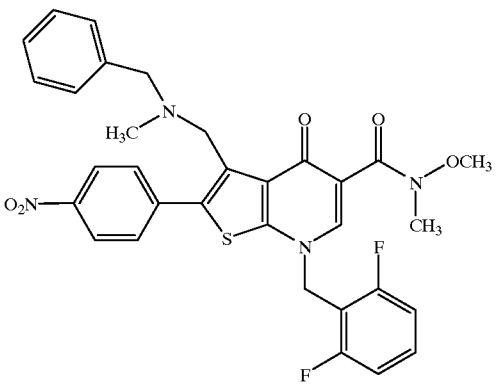

Yield: 96% mp 100–102° C.

Reference Example 27

Production of 4,7-dihydro-7-(2,6-difluorobenzyl)-2-(4-nitrophenyl)-5-benzoyl-3-methyl-4-oxothieno[2, 3-b]pyridine The compound obtained in Reference Example 18 (3.93 g, 7.87 mmol) was dissolved in anhydrous tetrahydrofuran (THF) (300 ml) with slightly warming. While this solution was kept at 0° C., a solution of phenyl magnesium bromide in THF (1 M, 15.7 ml, 15.7 mmol) was added dropwise to the mixture over 10 minutes. After the addition was completed, the solution was stirred for further 1 hour. The reaction mixture was partitioned between ethyl acetate (300 ml) and water (50 ml), and then the water layer was again extracted with ethyl acetate. The combined organic layers were dried with magnesium sulfate, the solvent was concentrated under reduced pressure to yield a residue, which was chromatographed on silica gel to yield yellow crystals (3.00 g, 74%), which was then recrystallized from ethyl acetate-hexane to give yellow crystals.

mp 114–116° C. Elemental analysis for $C_{28}H_{18}N_2O_4SF_2$ $0.7H_2O$; C(%), H(%), N(%), Calculated 63.56; 3.70; 5.29; Found 63.83; 3.95; 5.08; H-NMR (500 MHz, $CDCl_3$) δ: 2.68(3H, s), 5.30(2H, s), 7.02(2H, t, J=8.1 Hz), 7.43(3H, t, J=7.2 Hz), 7.52–7.63(3H,m), 7.86(2H, d, J=7.5 Hz), 7.99 (1H, s), 8.30(2H, d, J=8.7 Hz). IR (KBr): 3422, 3068, 1665, 1615, 1491, 1473, 1346, 853 $cm^{-1}$. FAB-Mass m/z 517 $(MH)^+$ Reference Example 28

Production of 3-(N-benzyl-N-methylaminomethyl)-4,7-dihydro-7-(2,6-difluorobenzyl)-2-(4-aminophenyl)-5-benzoyl-4-oxothieno[2,3-b]pyridine To a mixture of the compound obtained in Reference Example 23-1 (0.30 g, 0.47 mmol) in ethyl alcohol (6 ml) were added water (2 ml), and then one drop of concentrated hydrochloric acid was added to yield a uniform solution. To this solution were added iron powder (0.105 g, 2.0 mmol) and concentrated hydrochloric acid (0.39 ml, 4.7 mmol) carefully. After the addition was completed, the mixture was stirred at room temperature for 5 hours and filtered through Celite. A small amount of aqueous ammonia was added, and then the reaction filtrate was concentrated under reduced pressure. The obtained residue was poured into ice water, neutralized with sodium bicarbonate, and extracted with ethyl acetate. After the combined organic layers were washed with saline, and dried ($MgSO_4$), the solvent was distilled off under reduced pressure. The obtained residue was chromatographed on silica gel and recrystallized from isopropyl ether to yield yellow needles (0.24 g, 84%).

mp 126–128° C. Elemental analysis for $C_{36}H_{29}N_3O_2SF_2$ $1/2H_2O$; C(%), H(%), N(%), Calculated: 68.93; 5.04; 6.70; Found: 68.71; 5.18; 6.62; $^1$H-NMR (300 MHz, $CDCl_3$) δ: 2.13 (3H, s) 3.65 (2H, s), 3.87 (2H, br s), 4.14(2H, s), 5.28(2H, s), 6.74(2H, d, J=8.7 Hz), 7.00(2H, t, J=7.8 Hz), 7.16–7.24(5H, m), 7.36–7.46(3H, m), 7.53(1H, t, J=7.2 Hz), 7.62(2H, d, J=8.4 Hz), 7.89(2H, d, J=7.2 Hz), 7.94(1H, s). IR (KBr): 3358, 1607, 1495, 1473, 1035 $cm^{-1}$. FAB-Mass m/z 606$(MH)^+$ Reference Example 29

Production of 2-(4-aminophenyl)-7-(2,6-difluorobenzyl)-4,7-dihydro-5-isobutyryl-3-(N-benzyl-N-methylaminomethyl)-4-oxothieno[2,3-b]pyridine

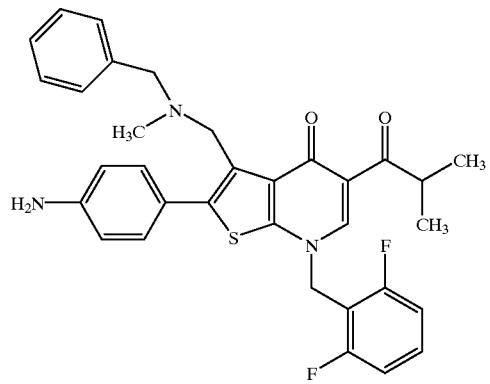

To a solution of the compound obtained in Reference Example 23-2 (0.25 g, 0.415 mmol) in methanol (5 ml) were added dropwise iron powder (0.093 g, 1.66 mmol) and concentrated hydrochloric acid (0.8 ml) with ice cooling. After the addition was completed, the mixture was stirred at room temperature for 1 hour and filtered through Celite. A small amount of a saturated aqueous solution of sodium hydrogen carbonate (10 ml) was added, followed by extraction with methylene chloride (30 ml×3). The combined extracts were washed with saline, and dried ($MgSO_4$), the solvent was distilled off under reduced pressure. The obtained residue was chromatographed on silica gel to yield light yellow amorphous powders (0.203 g, 861).

$^1$H-NMR(300 MHz,$CDCl_3$)δ: 1.18(6H, d), 2.11(3H, s), 3.65(2H, s), 3.85(2H, br s), 4.17(2H, s), 4.18(1H, m), 5.25(2H, s), 6.73(2H. d), 6.95(2H, t), 7.10–7.26(5H, m), 7.42(1H, m), 7.58(2H. d), 8.27(1H, s).

Reference Example 30

Production of 5-benzoyl-7-(2,6-difluorobenzyl)-4,7-dihyrdro-3-(N-benzyl-N-methylaminomethyl)-2-(4-propionylaminophenyl)-4-oxothieno[2,3-b]pyridine The compound obtained in Reference Example 28 (0.14 g, 0.23 mmol) was dissolved in anhydrous methylene chloride (2 ml), and then to the mixture was added triethylamine (0.038 ml) with ice cooling (0° C). After this solution was stirred for a while, to the mixture was added propionyl chloride (0.021 ml, 0.243 mmol). After the addition was completed, the solution was further stirred with ice cooling (0° C.) for 40 minutes. The reaction mixture was partitioned between methylene chloride (25 ml) and very thinly overlaid water (10 ml). The water layer was again extracted with methylene chloride (25 ml). The combined organic layers were washed with saline, and dried ($MgSO_4$), the solvent was distilled off under reduced pressure. The solid obtained was recrystallized from ethyl acetate-isopropyl ether to yield yellow needles (0.10 g, 65%).

mp 226–228 ° C. Elemental analysis for $C_{39}H_{33}N_3O_3SF_2$ $0.7H_2O$; C(%), H(%), N(%), Calculated: 69.46; 5.14; 6.23; Found: 69.60; 5.18; 6.04;

Thus obtained compound was dissolved in ethyl acetate, and then a saturated solution of hydrogen chloride (HCl) in ether was added in equal to slightly excess amount, and then the crystal precipitated was recrystallized from isopropyl ether to yield light yellow needles (0.095 g, 61%).

mp 218–220° C. Elemental analysis for $C_{39}H_{33}N_3O_3SF_2$·HCl·3.5H$_2$O; C(%), H(%), N(%), Calculated: 61.53; 5.43; 5.52; Found: 61.83; 5.33; 5.30; $^1$H-NMR (300 MHz, DMSO-d$_6$) δ: 1.11(3H, t, J=7.2 Hz),1.93(3H, s),2.35(2H, q,J=7.5 Hz), 3.44(2H, s), 4.00(2H, s), 5.62(2H, s), 7.11–7.25 (6H, m), 7.43–7.72(10H, m), 7.79(2H, d, J=7.5 Hz), 8.40 (1H, s), 10.03(1H, s). IR (KBr): 3422,. 3068, 1603, 1502, 1473, 1035 cm$^{-1}$. FAB-Mass m/z 662(MH)$^+$

Reference Example 31

The following compounds (Reference Examples 31-1 through 31-10) were produced by the same method as described in Reference Example 30, using various acid chlorides, isocyanates, and chlorocarbonic acid esters in place of propionyl chloride, and also using the amines shown in Example 16 and carbonylduimidazole, with the compounds obtained in Reference Examples 28 and 29 as the starting materials. The following compounds (Reference Examples 31-11 through 31-16) can also be produced in the same manner.

Reference Example 31-1:

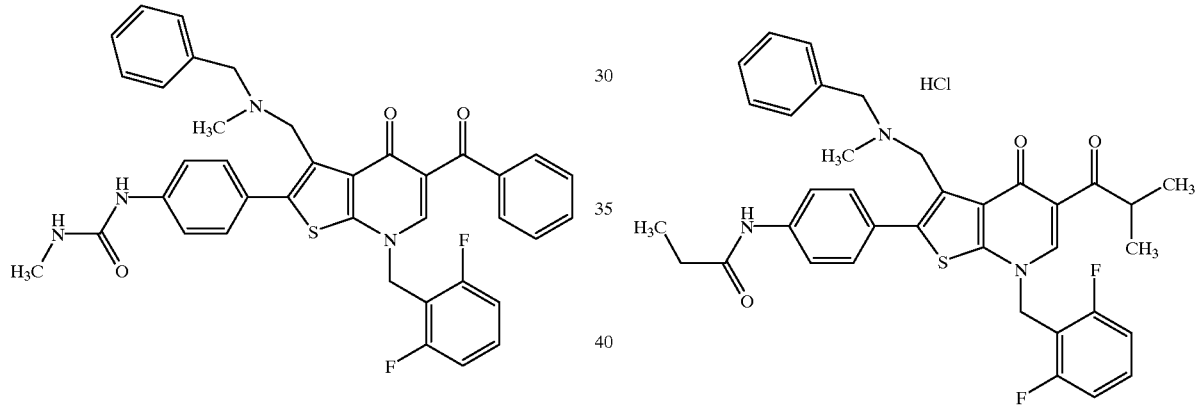

Yield: 68% mp 238–240° C.

Reference Example 31-1-2:

mp 230–232° C.

Reference Example 31-2-1:

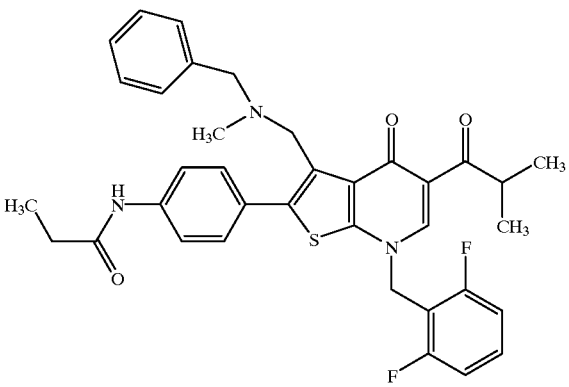

Yield: 64% mp 201–204° C.

Reference Example 31-2-2:

mp 207–214° C. Reference Example 31-3-1:

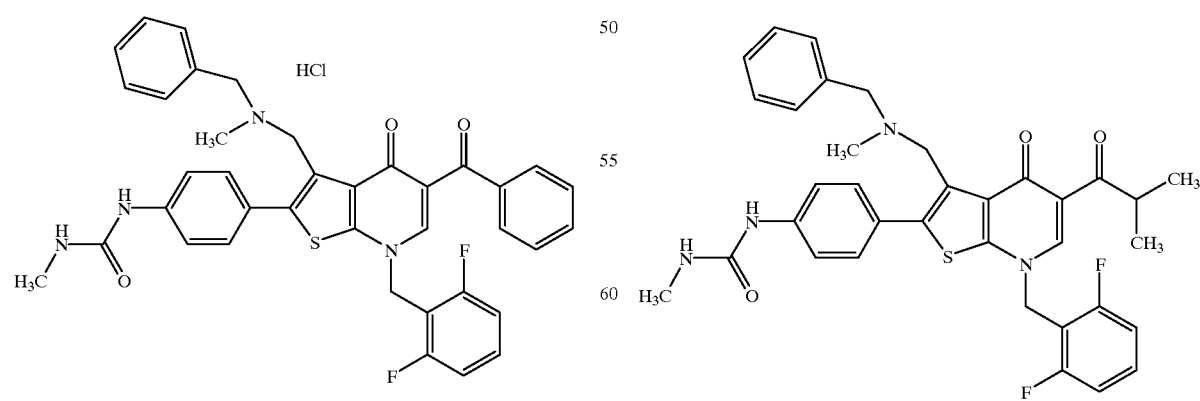

Yield: 55% mp 207–210° C.

Reference Example 31-3-2:
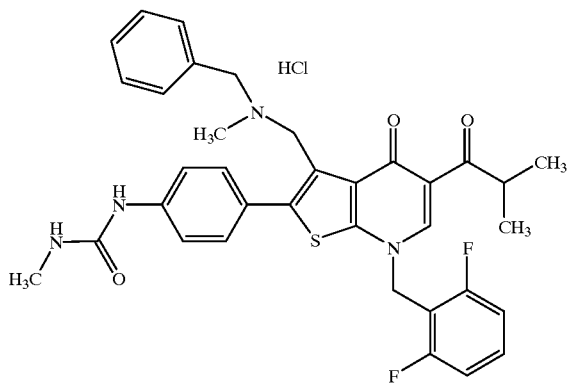
mp 222–226° C.
Reference Example 31-4:
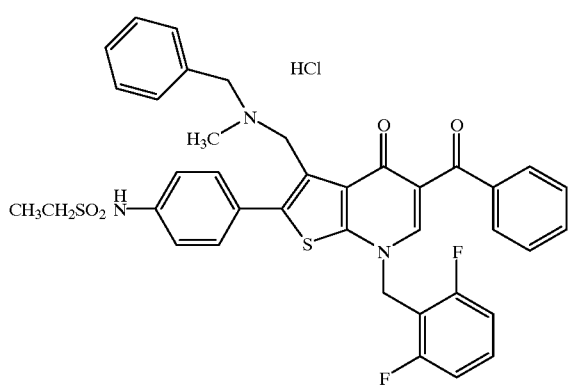
Yield: 49% mp 185–187° C.
Reference Example 31-5:
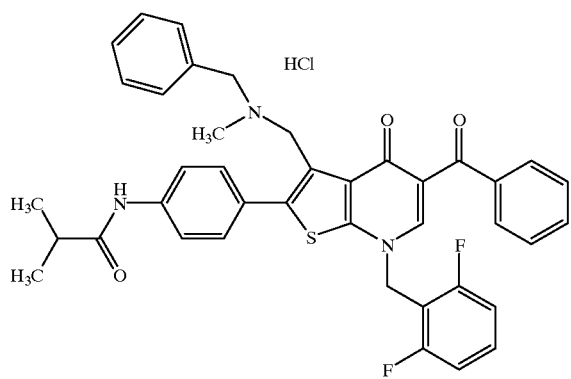
Yield: 79% mp 216–218° C.
Reference Example 31-6:
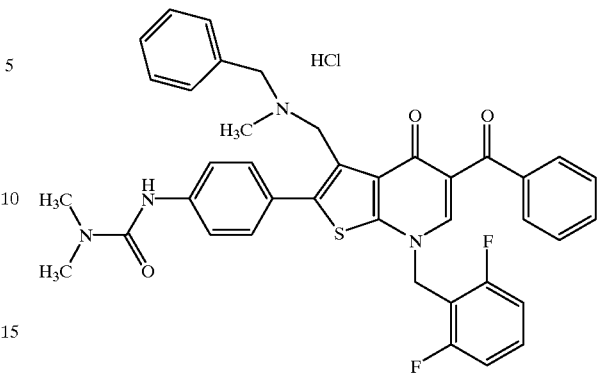
Yield: 73% mp 180–183° C.
Reference Example 31-7:
Yield: 65% mp 245–247° C.
Reference Example 31-8:
Yield: 65%

Reference Example 31-9:
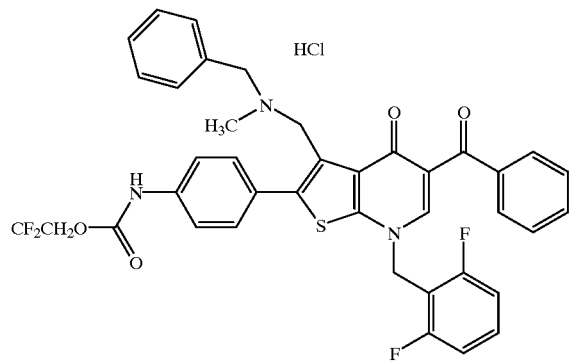
Yield: 70% mp 232–234° C.
Reference Example 31-10:
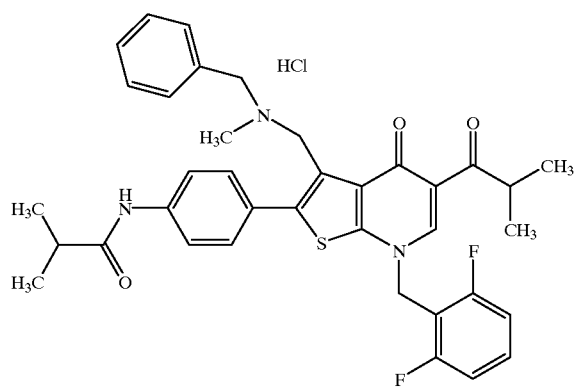
Yield: 73% mp 192–197° C.
Reference Example 31-11:
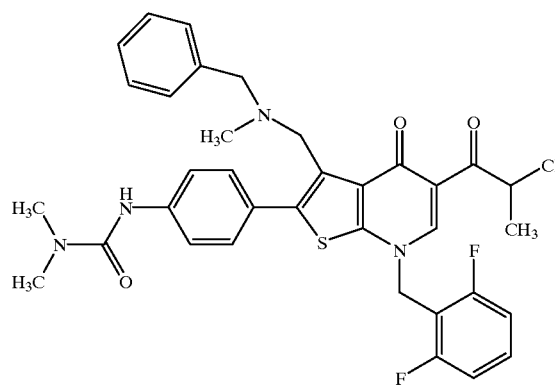
Reference Example 31-12:
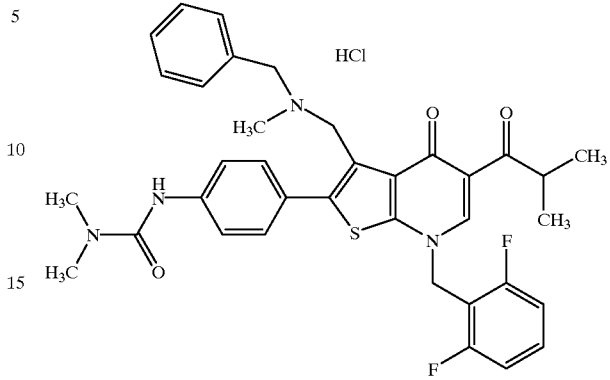
Reference Example 31-13:
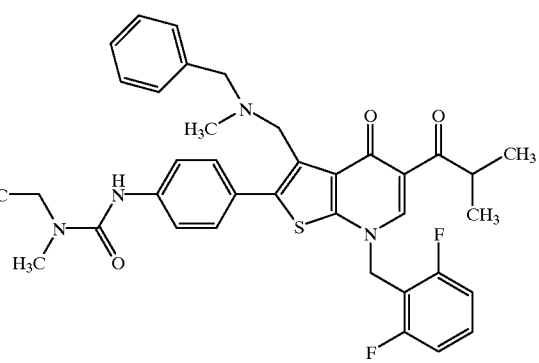
Reference Example 31-14:
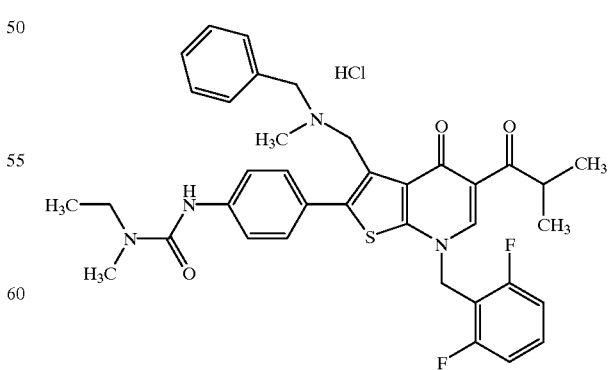

Reference Example 31-15:

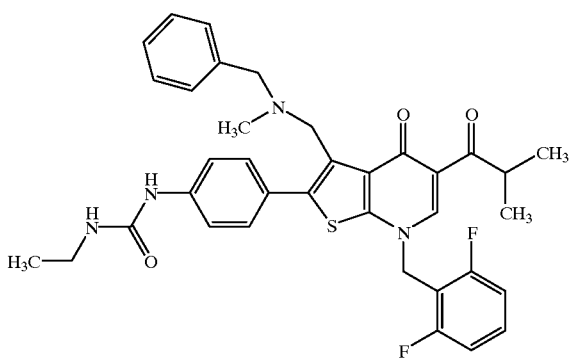

Reference Example 31-16:

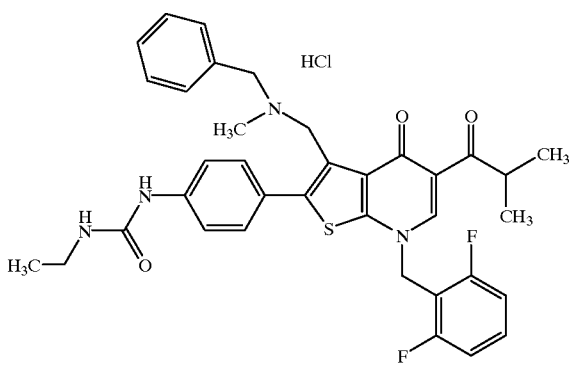

Reference Example 32

Production of 3-(N-benzyl-N-methylaminomethyl)-4,7-dihyrdro-7-(2,6-difluorobenzyl)-2-(4-nitrophenyl)-5-benzoyl-4-oxothieno[2,3-b]pyridine The compound obtained in Reference Example 26 (1.91 g, 3.09 mmol) was dissolved in anhydrous tetrahydrofuran (THF) (30 ml) with warming, and then to the mixture was added dropwise a solution of phenyl magnesium bromide in THF (1 M, 6.18 ml, 6.2 mmol) with ice cooling (0° C.) over 10 minutes. After stirring under ice cooling conditions for 1 hour, the reaction mixture was partitioned between ethyl acetate (100 ml) and aqueous hydrochloric acid (0.5 N, 100 ml), and then the organic layer was again washed with saturated saline (100 ml). After the organic layer was dried (MgSO$_4$), the solvent was distilled off under reduced pressure. The obtained residue was chromatographed on silica gel to yield yellow crystals (1.00 g, 51%), which was then recrystallized from isopropyl ether to yield yellow needles.

mp 197–199° C. Elemental analysis for $C_{36}H_{27}N_3O_4SF_2$ 0.7H$_2$O; C(%), H(%), N(%), Calculated: 66.70; 4.42; 6.48; Found: 66.59; 4.48; 6.42; $^1$H-NMR (300 MHz, CDCl$_3$) δ: 2.17(3H, s), 3.61(2H, s), 4.16(2H, s), 5.30(2H, s), 7.03(2H, t, J=8.1 Hz), 7.19–7.25(5H, m), 7.40–7.47(3H, m), 7.56(1H, t, J=7.5 Hz), 7.88 (2H, d, J=6.9 Hz), 7.96(1H, s), 8.10(2H, d, J=8.7 Hz), 8.28(2H, d, J=8.7 Hz). IR (KBr): 3430,1663, 1611, 1518, 1473, 1348, 853 cm$^{-1}$. FAB-Mass m/z 636 (MH)$^+$

Reference Example 33

Production of 3-(N-benzyl-N-methylamlnomethyl)-4,7-dihyrdro-7-(2,6-difluorobenzyl)-2-(4-isobutyrylaminophenyl)-5-m(2-bromoisobutyryl)o-4-oxothieno2,3-b]pyridine The compound obtained in Reference Example 31-10 (0.48 g, 0.75 mmol) was dissolved in dichloromethane (15 ml). To the solution was added dropwise 47% hydrotromic acid (0.35 ml, 3.0 mmol) at room temperature for 1 minutes, followed by further stirring for 10 minutes. To this reaction mixture was added dropwise bromine (39 μl, 0.75 mmol), followed by further stirring at room temperature for 24 hours. The reaction mixture was partitioned between dichloromethane (30 ml) and aqueous sodium bicarbonate (saturated, 60 ml), and then the organic layer was again washed with saturated saline (100 ml). After the organic layer was dried (MgSO$_4$), the solvent was distilled off under reduced pressure to yield brown amorphous crystals (0.53 g).

Reference Example 34

Production of 3-(N-benzyl-N-methylaminomethyl)-4,7-dihyrdro-7-(2,6-difluorobenzyl)-2-(4-isobutyrylaminophenyl)-5-methacryloyl-4-oxothieno[2,3-b]pyridine The compound obtained in Reference Example 33 (0.52 g, 0.72 mmol) was dissolved in dimethylformamide (DMF) (30 ml), and then to this solution was added potassium actate (2.30 g, 20 mmol) at room temperature, followed by stirring at 100° C. for 20 hours. There action mixture was partitioned between ethyl acetate (30 ml) and water (30 ml), and then the water layer was again washed with ethyl acetate (10 ml). The combined organic layers were again washed with saturated saline (30 ml). After the organic layer was dried (MgSO$_4$), the solvent was distilled of f under reduced pressure to yield a brown oil (0.56 g).

Example 1

Example 1-1

Production of 3- (N-benzyl-N-methylaminomethyl)-4,7-dihydro-5-isobutyryl-7-(2,6-difluorobenzyl) -2-(4-acyclopropanecarbonylaminophenyl)-4-(oxothieno[2,3-b]pyridine

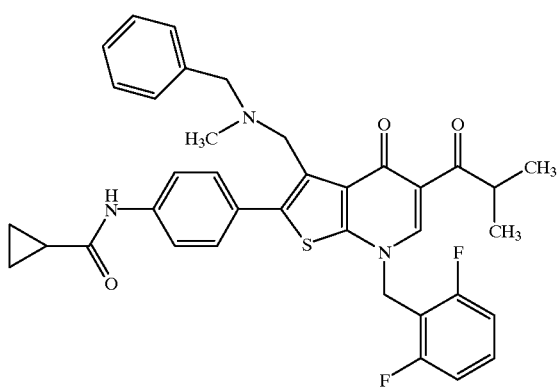

To a solution of the compound obtained in Reference Example 29 (2.57 g, 4.5 chnol) in dichioromethane (50 ml) were added cyclopropanecarboxylic acid (861 mg, 10 mmol) and diisopropylethylamine (2.59 9m 20 mmol), and then benzotriazol-1-yl-oxy tripyrrolidino phosphohium hexafluorophosphoric acid (PyBop) (5. 40 g, 10 mmol) was added to it in a small portion with ice cooling. After stirring at room temperature for 1 day, the reaction mixture was poured into a 0.1 N aqueous solution of potassium hydroxide and extracted with chloroform. The combined extracts were washed with saline, and dried ($Na_2SO_4$), the solvent was distilled off under reduced pressure. The obtained residue was chromatographed on silica gel and recrystallized from ethyl acetate to yield white powdery crystals (2.15 g, 79%).

$^1$H-NMR (300 MHz, $CDCl_3$) 8: 0.85–0.90(2H, m), 1.10–1.15(2H,mu), 1.18(6H, d), c.3–1.59(1H,em), 2.09(3H, s), 4.12–4.20(1H, m), 4.16(2H, s), 5.25(2H, s)5 6.99(2H, t), 7.10–7.25(6H, m), 7.35–7.45(1H, m), 7.61(2H, d), 7.67(1H, br s), 7.76(2H, d), 8.27(1H, s).

FAB-Mass m/z 608(MH)$^+$

Example 1-2

Production of 3-(N-benzyl-N-methylaminomethyl)-4,7-dihydro-5-isobutyryl-7-(2,6-difluorobenzyl)-2-(4-cyclopropanecarbonylaminophenyl) -4-oxothieno[2,3-b]pyridine hohydrochloride

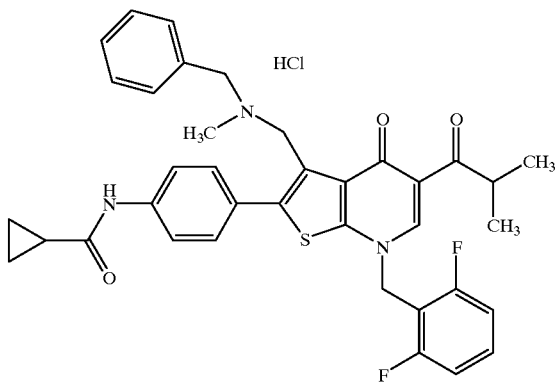

The white powdery crystals obtained in Example 1-1 were dissolved in ethanol, and then a solution of hydrogen chloride in ethyl ether was added to it in a small excess amount, followed by recrystallization from ethanol-ethyl ether, to yield white powdery crystals (2.20 g, 72%).

mp 254–256° C. Elemental analysis for $C_{37}H_{35}N_3O_3SF_2$ HCl; C(%), H(%), N(%), Calculated: 65.72; 5.37; 6.21; Found: 65.61; 5.38; 6.25; IR (KBr): 2950, 1673, 1595, 1502, 1473, 1408, 1313, 11830cm6$^{-1}$.

Example 2

Production of 4,7-dihydro-2-(4-(3-acetoxy-2-ethydpropionylamino)phenyl]-7-(2,6-difluorobenzyl)-3-(N-benzyl-N-methylaminomethyl) -5-isobutyryl-4-oxothieno[2,3-b]pyridine

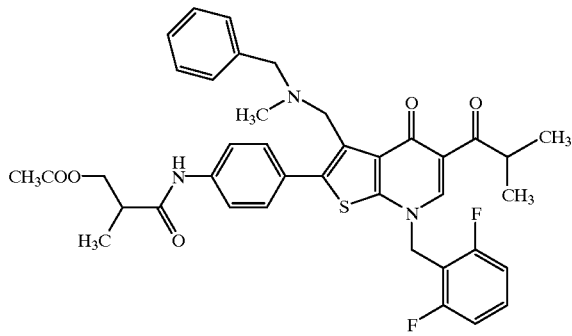

To a solution of the compound obtained in Reference Example 29 (1.14 g, 2.0 mnmol) in dichioromethane (30 ml) were added dropwise triethylamine (500 mg, 5 mmnol) and 3-acetoxy isobutyryl chloride (0.5 g, 3 mmol) with ice cooling over 1 minute, followed by further stirring at room temperature for 1 hour. The reaction mixture was partitioned between a saturated aqueous solution of sodium hydrogen carbonate (30 ml) and dichloromethane (30 ml), and then the water layer was again extracted with dichloromethane (10 ml). The combined extracts were washed with saline, and dried ($Na_2SO_4$), the solvent was distilled off under reduced pressure. The obtained residue was chromatographed on silica gel to yield brown crystals (1.4 g).

$^1$H-NMR (300 MHz, $CDCl_3$) δ: 1.18(6H,d), 1.30(3H,d), 2.08(3H,s), 2.12(3H,s), 2.73–2.84(1H,m), 3.65(2H,s), 4.11–4.36(3H,m), 4.17(2H,s), 5.27(2H,s), 7.00(2H,t), 7.13–7.22(5H,m), 7.36–7.46(1H,m), 7.52(1H,br s), 7.62–7.82(4H,q), 8.29(1H, s).

Example 3

Production of 3-(N-benzyl-N-methylaminomethyl)-4,7-dihydro-5-isobutyryl-7-(2,6-difluorobenzyl)-2-[4-(3-hydroxy-2-methylpropionylamino)phenyl]-4-oxothieno[2,3-b]pyridine

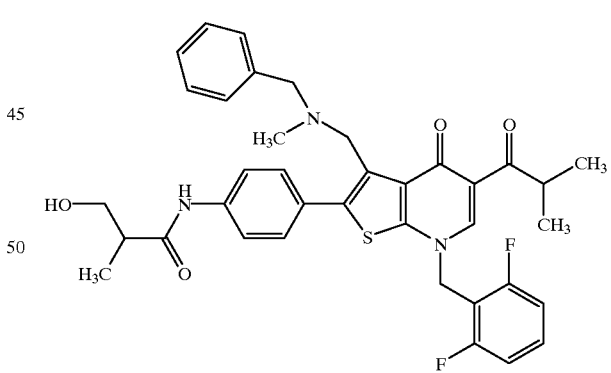

The compound obtained in Example 2 (1.40 g) was dissolved in methanol (100 ml), and then to the solution was added potassium carbonate f2.0 g, 15 mmol), followed by stirring at room temperature for 15minutes. The reaction mixture was partitioned between ethyl acetate (200 ml) and distilled water (300 ml), and then the water layer was extracted with ethyl acetate (100 ml). The combined extracts were washed with saline, and dried ($Na_2SO_4$), the solvent was distilled off under reduced pressure. The obtained residue was chromatographed on silica gel and recrystallized from ether to yield white crystals (0.95 g, 72%).

mp 161–162° C. Elemental analysis for $C_{37}H_{37}N_3O_4SF_2$ 0.5H$_2$O; C(%), H(%), N(%), Calculated: 66.65; 5.74; 6.30; Found: 66.70; 5.52; 6.40; $^1$H-NMR (300 MHz, CDCl$_3$) δ: 1.17(6H,d), 1.18(3H,d), 2.06(3H,s), 2.67–2.78(1H,m), 3.61 (2H,s), 3.57–3.84(2H,m), 3.99–4.08(1H,m), 4.15(2H,s), 5.52(2H,s), 7.08(2H,t), 7.15(5H,s), 7.44–7.54(1H,m), 7.58 (2H,d), 7.69(2H,d), 8.46(1H, s).

FAB-Mass m/z 658(MH)$^+$

Example 4

Using the compound obtained in Reference Example 29, the following compounds (Examples 4-1 to 4-3) were obtained in the same manner as in Example 1.

Example 4-1

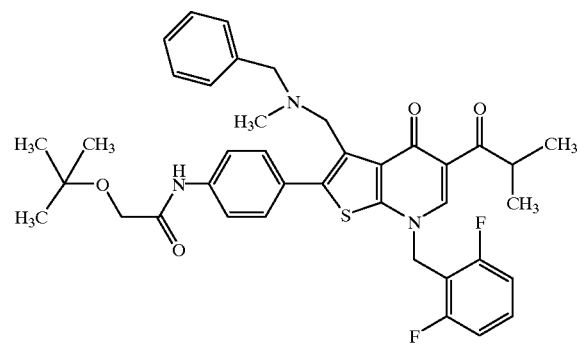

Yield: 67% mp 201–203° C.

Example 4-2

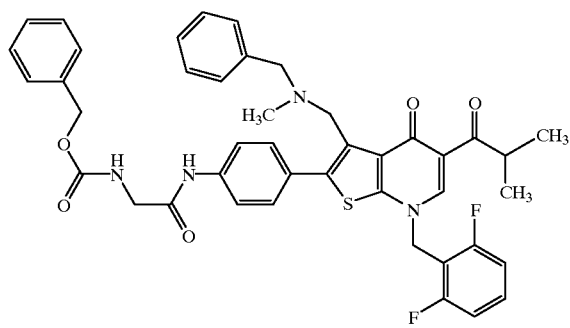

Yeld: 58%: mp 135–137° C.

Example 4-3

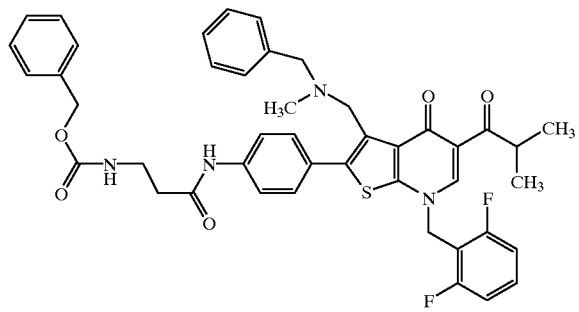

Yield: 751% mp 205–207° C.

Example 5

Example 5-1

Production of 3-(N-benzyl-N-methylaminomethyl)-4,7-dihydro-7-(2,6-difluorobenzyl)-2-[4-(2-hydroxyacetylamino)phenyl]-5-isobutyryl-4-oxothieno[2,3-b]pyridine

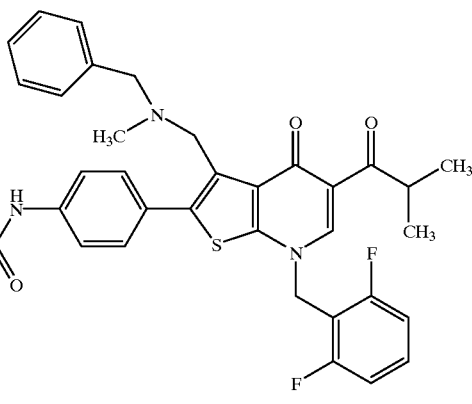

The compound obtained in Example 4-1 (0.137 g) was dissolved in dichloromethane (1.0 ml), and then to the solution was added dropwise trifluoroacetic acid (1.0 ml) with ice cooling. After stirring under ice cooling conditions for 1 hour, the reaction mixture was concentrated to dryness under reduced pressure, and then the obtained residue was partitioned between chloroform (50 ml) and saturated aqueous sodium bicarbonate (50 ml), and then the water layer was again extracted with chloroform (10 ml). The combined organic layers were washed with saturated saline (30 ml). After the organic layer was dried (MgSO$_4$), the solvent was distilled off under reduced pressure, and then the obtained residue was chromatographed on silica gel and recrystallized from ethanol-ethyl acetate-ethyl ether to yield white crystalline powders (0.12 g, 95%).

Example 5-2

Production of 3-(N-benzyl-N-methylaminomethyl)-4,7-dihydro-7-(2,6-difluorobenzyl)-2-[4-(2-hydroxyacetylamino)phenyl]-5-isobutyryl-4-oxothieno[2,3-b]pyridine hydrochloride

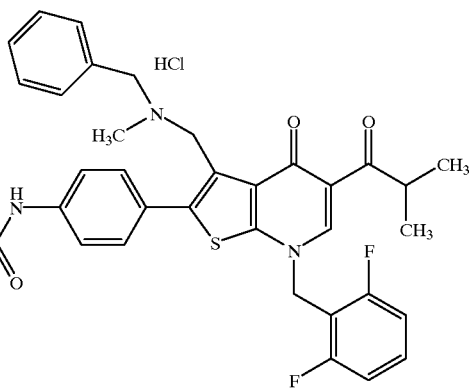

The white crystalline powders obtained in Example 5-1 were dissolved in dichloromethane (1.0 ml), and then to this solution was added an ethanolic solution containing 10 N hydrogen chloride1(.0 ml) with ice cooling. The solvent was distilled off under reduced pressure, and then the residue was recrystallized from ethanol-ethyl acetate to yield white crystalline powders (0.12 g, 84%).

mp 197–199° C. Elemental analysis for $C_{35}H_{33}N_3O_4SF_2$ HCl 2.5H$_2$O; C(%), H(%), N(%), Calculated: 59.11; 5.53; 5.91; Found: 59.06; 5.25; 5.93; $^1$H-NMR(300 MHz, CDCl$_3$) δ: 1.18(6H, d), 2.10(3H, s), 3.63(2H,s), 3.72(1H,br), 4.09–4.17(1H,m), 4.16(2H,s), 4.24(2H,s), 5.24(2H,s), 6.99 (2H,t), 7.18–7.23(5H,m), 7.35–7.45(1H,m), 7.63(2H,d), 7.73(2H,d), 8.25(1H,s), 8.59(1H,s).

Example 6

Using the compounds obtained in Example 4-2 and Example 4-3, the following compounds (Examples 6-1 to 6-2) were obtained in the same manner as in Example 5.
Example 6-1:

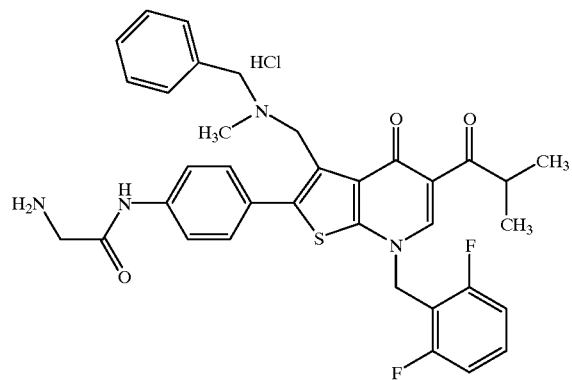

Yield: 76% mp 192–194° C.

Example 6-2

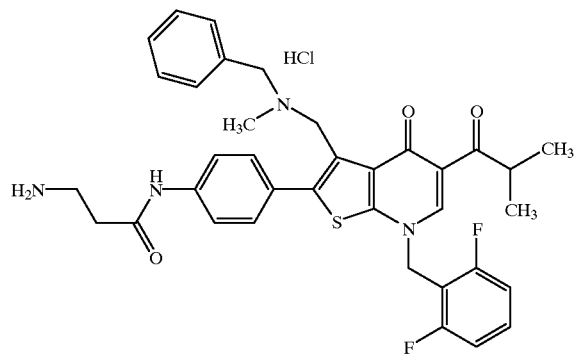

Yield: 81% mp 193–195° C.

Example 7

Production of 3-(N-benzyl-N-methylaminomethyl)-4,7-dihydro-7-(2,6-difluorobenzyl)-2-(4-isobutyrylaminophenyl)-5-(2-hydroxy-2-methylpropionyl)-4-oxothieno[2,3-b]pyridine

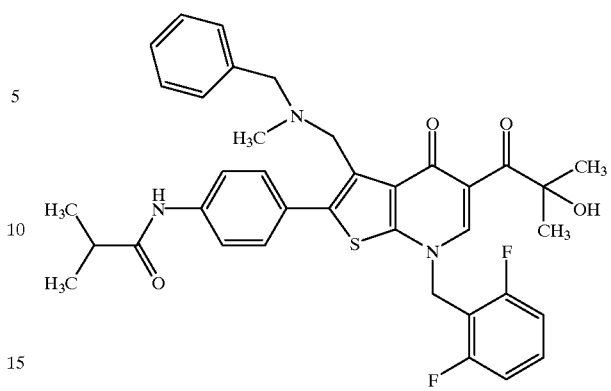

The brown amorphous crystal (0.13) obtained by repeating the method described in Reference Example 33 using the compound obtained in Reference Example 31-10 was hydrolyzed with potassium acetate by the same method as described in Reference Example 34 The solid obtained was chromatographed on silica gel to remove the compound obtained in Reference Example 34, an d the by product was recrystallized from methanol to yield colorless crystalline powders (0.03 g).

mp 170–172° C. Elemental analysis for $C_{37}H_{37}N_3O_4SF_2$ 1/6H$_2$O; C(%), H(%), N(%), Calculated: 67.26; 5.69; 6.36; Found: 67.18; 5.74; 6.46; $^1$H-NMR (300 MHz, CDCl$_3$) δ: 1.28(6H,d), 1.49(6H,s), 2.06(3H,s), 2.51–2.60(1H,m), 3.61 (2H,s), 4.13(2H,s), 5.31(2H,s), 7.01(2H,t), 7.12–7.21(5H, m), 7.37–7.47(2H,m), 7.64(2H,d), 7.74(2H,d), 8.04(1H,s), 8.35(1H,s). IR (KBr): 3466,1669, 1499, 1313, 1075 cm$^{-1}$.

Example 8

Production of 3-(N-benzyl-N-methylaminomethyl)-4,7-dihydro-7-(2,6-difluorobenzyl)-2-(4-isobutyrylaminophenyl)-5-(3-hydroxy-2-methylpropionyl)-4-oxothieno[2,3-b]pyridine

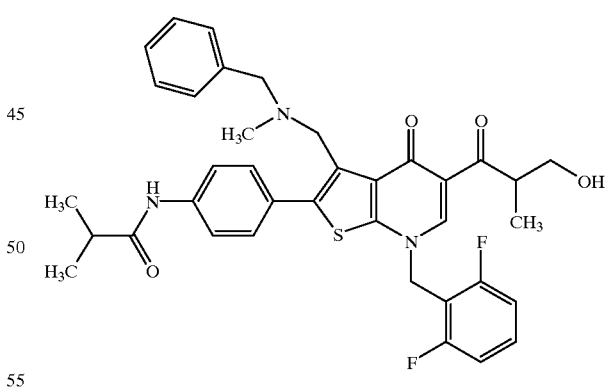

The compound obtained in Reference Example 34 (0.56 g) was dissolved in trifluoroacetic acid (10 ml) and stirred at room temperature for 1 hour. The reaction mixture was concentrated to dryness under reduced pressure, and the obtained residue was partitioned between dichloromethane (30 ml) and saturated aqueous sodium bicarbonate (60 ml), and then the water layer was again extracted with dichloromethane (10 ml). The combined organic layers were washed with saturated saline (30 ml). After the organic layer was dried (MgSO$_4$), the solvent was distilled off under reduced pressure to yield brown amorphous crystals (0.42 g), which was chromatographed on silica gel to yield yellow crystals (0.07 g, overall recovery rate as calculated from the compound obtained in Reference Example 31-10 12%).

¹H-NMR (300 MHz, CDCl₃) δ: 1.15(3H,d), 1.26(6H, d), 2.07(3H, s), 2.53–2.62(1H, m), 3.58(2H, d), 3.66(2H, d), 3.82(1H, dd), 3.93(1H, dd), 4.03(1H, d), 4.22(1H, d), 4.27–4.37(1H, m), 5.26(2H, s), 6.99(2H, t), 7.13–7.21(5H, m), 7.36–7.46(1H,m), 7.63(2H, d), 7.67(2H, d), 7.79(1H, s), 8.30(1H, s).

Example 9

Production of (R)-4,7-dihydro-2-[4-(3-t-butoxy-2-methylpropionylamino)phenyl]-7-(2,6-difluorobenzyl)-3-(N-benzyl-N-methylaminomethyl)-5-isobutyryl-4-oxothieno[2,3-b]pyridine

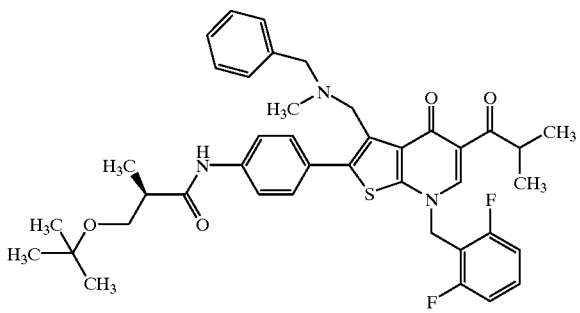

To a solution of the compound obtained in Reference Example 29 (1.14 g, 2.0 mmol) in dichloromethane (20 ml) were added diisopropylethylamine (520 mg, 4 mmol) and (2R)-3-t-butoxy-2-methylpropanoic acid (0.43 g, 3 mmol), followed by stirring with ice cooling. To this solution was added benzotriazol-1-yloxytrisdimethylaminophosphonium hexafluorophosphate (BOP reagent) (1.33 g, 3 mmol). After stirring with ice cooling for 1 hour, the solution was further stirred at room temperature for 4 hours. The reaction mixture was concentrated to dryness under reduced pressure, and then the obtained residue was partitioned between water (50 ml) and chloroform (50 ml). The water layer was again extracted with chloroform (10 ml). The combined extracts were washed with saline, and dried (MgSO₄), the solvent was distilled off under reduced pressure. The obtained residue was chromatographed on silica gel to yield yellow powders (1.11 g, 786).

¹H-NMR (300 MHz, CDCl₃) δ: 1.18(6H,d), 1.25(3H,d), 1.30(9H,s), 2.62(3H,s), 2.63–2.71(1H,m), 3.51(1H,t like), 3.61(1H,dd), 3.64(2H,s), 4.18(2H,s), 4.18(1H,quint), 5.27 (2H,s), 7.00(2H,t), 7.14–7.22(5H,m), 7.36–7.46(1H,m), 7.60(2H,d), 7.76(2H,d), 8.28(1H, s), 9.00(1H,s).

Example 10

Example 10-1

Production of (R)-4,7-dihydro-2-[4-(3-hydroxy-2-methylpropionylamino)phenyl]-7-(2,6-difluorobenzyl)-3-(N-benzyl-N-methylaminomethyl)-5-isobutyryl-4-oxothieno[2,3-b]pyridine

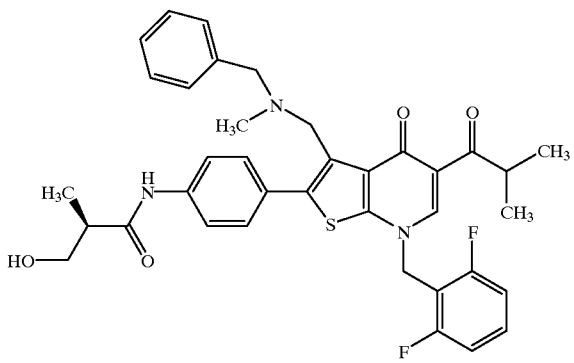

The compound obtained in Example 9 (1.11 g) was dissolved in trifluoroacetic acid (5 ml) under ice cooling conditions, and then after stirring for 1 hour, the solution was allowed to warm to room temperature and stirred for further 12 hours. The reaction mixture was concentrated to dryness under reduced pressure, and then the residue was dissolved in methanol (20 ml) and again cooled with ice, and then a 5 N solution of sodium hydroxide was added to reach pH 9.0. The reaction mixture was stirred for 30 minutes and further stirred at room temperature for 30 minutes. The reaction mixture was concentrated to dryness under reduced pressure at low temperature, and then the obtained residue was chromatographed on silica gel. The light yellow amorphous crystals obtained (0.83 g, 82%) were recrystallized from ether to yield light yellow powdery crystals (0.69 g).

mp 161–162° C. Elemental analysis for C₃₇H₃₇N₃O₄SF₂ 0.5H₂O; C(%), H(%), N(%), Calculated 66.65; 5.74; 6.30; Found 66.47; 5.73; 6.10; ¹H-NMR (300 MHz, CDCl₃) δ: 1.18(6H,d), 1.28(3H,d), 2.11(3H,s), 2.71(1H,m), 3.65(2H, s), 3.83–3.85(2H,m), 4.16(1H,quint), 4.18(2H,s), 5.27(2H, s), 7.00(2H,t), 7.14–7.23(5H,m), 7.36–7.44(1H,m), 7.64 (2H,d), 7.77(2H,d), 8.09(1H, s), 8.28(1H,s). FAB-Mass m/z 658(MH)⁺

Example 10-2

Production of (R)-4,7-dihydro-2-[4-(3-hydroxy-2-methylpropionylamino)phenyl]-7-(2,6-difluorobenzyl)-3-(N-benzyl-N-methylaminomethyl)-5-isobutyryl-4-oxothieno[2,3-b]pyridine hydrochloride

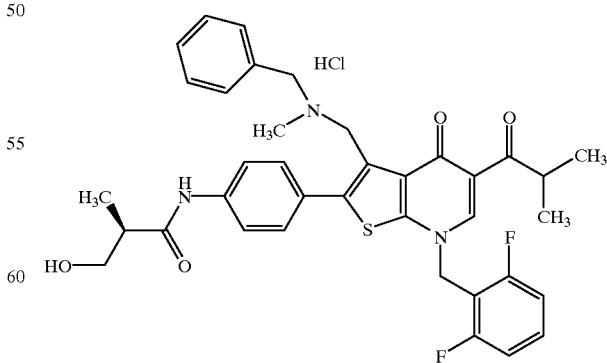

The title compound was obtained in the same manner as in Example 1. mp 214–216° C.

Example 11

Example 11-1

Production of 4,7-dihydro-2-[4-(2-hydroxy-2-methylpropionylamino)phenyl]-7-(2,6-difluorobenzyl)-3-(N-benzyl-N-methylaminomethyl)-5-isobutyryl-4-oxothieno[2,3-b]pyridine

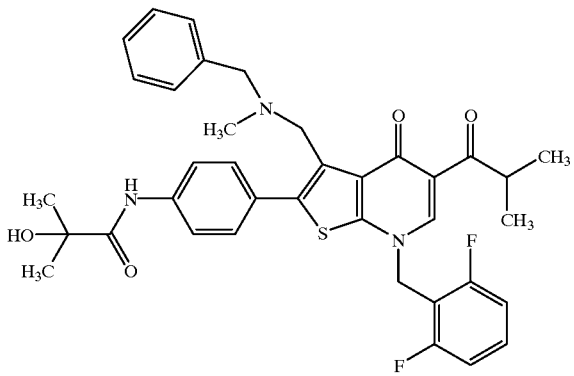

To a solution of the compound obtained in Reference Example 29 (1.14 g, 2.0 mmol) in dichloromethane (30 ml) were added diisopropylethylamine (1.04 g, 8 mmol) and 2-hydroxyisobutanoic acid (0.416 g, 4 mmol), followed by stirring under ice cooling conditions. To this solution was added benzotriazol-1-yloxytrisdimethylaminophosphonium hexafluorophosphate (BOP reagent) (1.76 g, 4 mmol). After stirring under ice cooling conditions for 1 hour, the solution was further stirred at room temperature for 4 days. The reaction mixture was concentrated to dryness under reduced pressure, and then the obtained residue was partitioned between water(50 ml)and chloroform(50 ml). The water layer was again extracted with chloroform (10 ml). The combined extracts were washed with saline, and dried (MgSO$_4$), the solvent was distilled off under reduced pressure. The obtained residue was chromatographed on silica gel and recrystallized from ether to yield yellow powdery crystal (6.56 g, 43%).

mp 178–180° C. Elemental analysis for C$_{37}$H$_{37}$N$_3$O$_4$SF$_2$ 0.5H$_2$O; C(%), H(%), N(%), Calculated: 66.65; 5.74; 6.30; Found 66.54; 5.49; 6.36; $^1$H-NMR (300 MHz, CDCl$_3$) δ: 1.18(6H,d), 1.58(6H,s), 2.10(3H,s), 3.05(1H,brs), 3.64(2H, s), 4.16(2H,s), 4.12–4.22(1H,m), 5.23(2H,s), 6.99(2H,t), 7.05–7.25(5H,m), 7.34–7.44(1H,m), 7.64(2H,d), 7.75(2H, d), 8.25(1H, s), 8.86(1H, s).

Example 11-2

Production of 4,7-dihydro-2-[4-(2-hydroxy-2-methylpropionylamino)phenyl]-7-(2,6-difluorobenzyl)-3-(N-benzyl-N-methylaminomethyl)-5-isobutyryl-4-oxothieno[2,3-b]pyridine hydrochloride

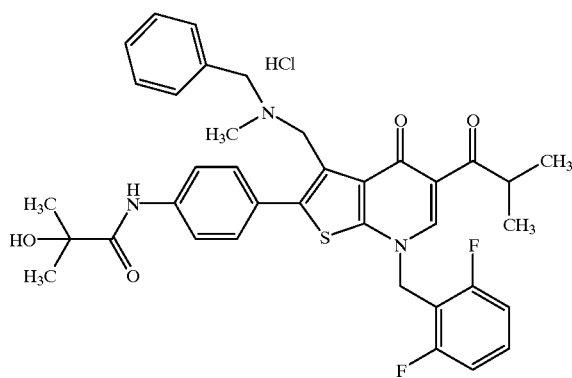

The title compound was obtained in the same manner as in Example 1. mp 213–215° C.

Example 12

Example 12-1

Production of 3-(N-benzyl-N-methylaminomethyl)-4,7-dihydro-5-isobutyryl-7-(2,6-difluorobenzyl)-2-[4-[(1-hydroxy cyclopropyl)carbonylaminolphenyl]-4-oxothieno[2,3-b]pyridine

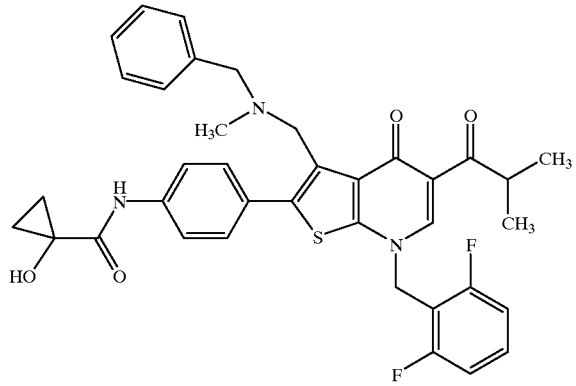

To a solution of the compound obtained in Reference Example 29 (0.57 g, 1.0 mmol) in dichloromethane (10 ml) were added diisopropylethylamine (0.52 g, 4 mmol) and 2-hydroxycyclopropanecarboxylic acid (0.204 g, 2 mmol), followed by stirring under ice cooling conditions. To this solution was added benzotriazol-1-yloxytrisdimethylaininophosphonium hexafluorophosphate (BOP reagent) (1.76 g, 4 mmol). After stirring under ice cooling conditions for 1 hour, the solution was further stirred at room temperature for 4 days. The reaction mixture was concentrated to dryness under reduced pressure, and then the obtained residue was partitioned between water (50 ml) and chloroform (50 ml). The water layer was again extracted with chloroform (10 ml). The combined extracts were washed with saline, and dried (MgSO$_4$), the solvent was distilled off under reduced pressure. The obtained residue was chromatographed on silica gel and recrystallized from ether to yield yellow powdery crystals (0.27 g, 41%).

$^1$H-NMR (300 MHz, CDCl$_3$)δ: 1.16–1.20(2H,m), 1.18 (6H,d), 1.48–1.51(2H,m), 2.09(3H,s), 3.64(2H,s), 3.95(1H, br s), 4.14(2H,s), 4.12–4.19(1H,m), 5.20(2H,s), 6.99(2H,t), 7.10–7.25(5H,m), 7.34–7.46(1H,m), 7.57(2H,d), 7.70(2H, d), 8.21(1H, s), 8.82(1H, s).

Example 12-2

Production of 3-(N-benzyl-N-methylaminomethyl)-4,7-dihydro-5-isobutyryl-7-(2,6-difluorobenzyl)-2-[4-[(1-hydroxy cyclopropyl)carbonylamino]phenyl]-4-oxothieno[2,3-b]pyridine hydrochloride

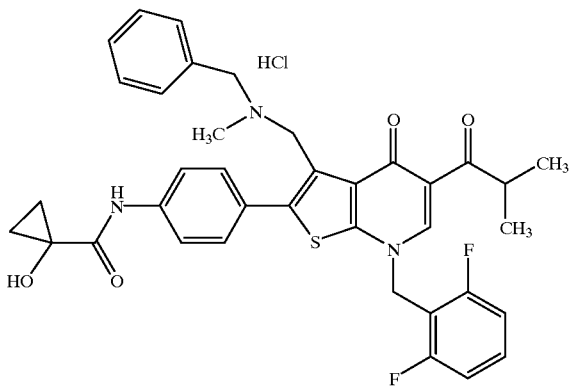

The title compound, white powdery crystals (0.12 g) was obtained in the same manner as in Example 1. Solvent for recrystallization: ethanol-ether mp 220–222° C. Elemental analysis for $C_{37}H_{35}N_3O_4SF_2$ HCl 0.5H$_2$O; C(%), H(%), N(%), Calculated: 63.37; 5.32; 5.99; Found: 63.35; 5.24; 5.82;

Example 13

Example 13-1

Production of 4,7-dihydro-2-[4-(3-hydroxy-3-methylbutyrylamino)phenyl]-7-(2,6-difluorobenzyl)-3-(N-benzyl-N-methylaminomethyl)-5-isobutyryl-4-oxothieno[2,3-b]pyridine

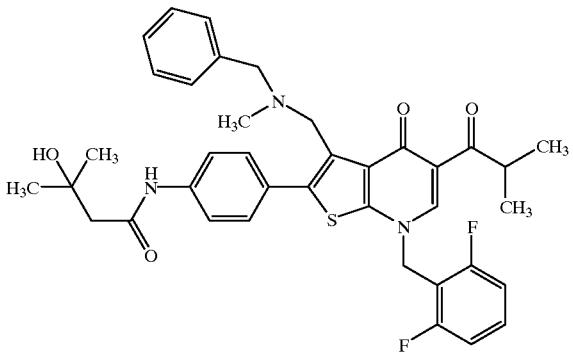

To a solution of the compound obtained in Reference Example 29 (1.14 g, 2.0 mmol) in dichloromethane (10 ml) were added diisopropylethylamine (1.04 g, 8 mmol) and 3-hydroxy-3-methylbutanoic acid (0.47 g, 4 mmol), followed by stirring under ice cooling conditions. To this solution was added benzotriazol-1-yloxytrisdimethylaminophosphonium hexafluorophosphate (BOP reagent) (1.76 g, 4 mmol). After stirring under ice cooling conditions for 1 hour, the solution was further stirred at room temperature for 4 days. The reaction mixture was concentrated to dryness under reduced pressure, and then the obtained residue was partitioned between water(50 ml)and chloroform(50 ml). The water layer was again extracted with chloroform (10 ml). The combined extracts were washed with saline., and dried (MgSO$_4$), the solvent was distilled off under reduced pressure. The obtained residue was chromatographed on silica gel and recrystallized from ether to yield yellow powdery crystals (0.50 g, 37%).

$^1$H-NMR (300 MHz, CDCl$_3$) δ: 1.17(6H,d), 1.39(6H,s), 2.11(3H,s), 2.58(2H,s), 3.12(1H, br s), 3.65(2H,s), 4.12–4.19(1H,m). 4.18(2H,s), 5.27(2H,s), 7.00(2H,t), 7.10–7.23(5H,m), 7.32–7.44(1H,m), 7.61(2H,d), 7.79(2H, d), 8.24(1H, s), 8.28(1H, s).

Example 13-2

Production of 4,7-dihydro-2-[4-(3-hydroxy-3-methylbutyryl amino)phenyl]-7-(2,6-difluorobenzyl)-3-(N-benzyl-N-methylaminomethyl)-5-isobutyryl-4-oxothieno[2,3-b]pyridine hydrochloride

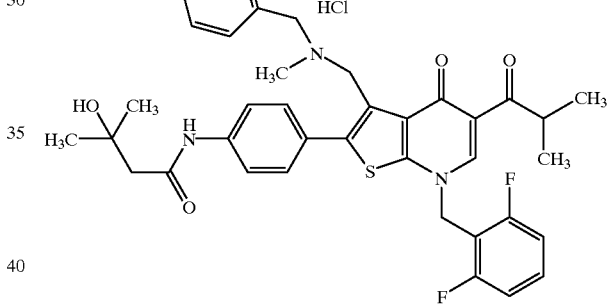

The title compound, white powdery crystals (0.42 g) were obtained in the same manner as in Example 1. Solvent for recrystallization: ethanol mp 216–218° C. Elemental analysis for $C_{38}H_{39}N_3O_4SF_2$ HCl H$_2$O; C(%), H(%), N(%), Calculated: 62.84; 5.83; 5.79; Found: 62.70; 5.75; 5.82;

Example 14

The following compounds (Examples 14-1 through 14-10) were produced by the same method as described in Examples 9, 11, 12, and 13, using the compound obtained in Reference Example 29, and also using various carboxylic acid compounds in place of, for example, (2R)-3-t-butoxy-2-methylpropanoic acid, which was used in Example 9.

Example 14-1
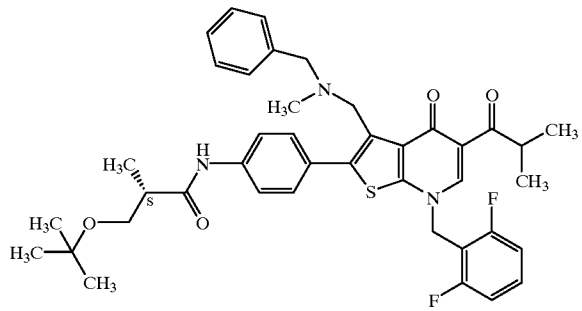
Yield: 46% Amorphous.
$^1$H-NMR (300 MHz, CDCl$_3$) δ: 1.18(6H,d), 1.25(3H,d), 1.30(9H,s), 2.11(3H,s), 2.60(1H,br), 3.51(1H, t like), 3.59–3.65(1H,m), 3.65(2H,s), 4.17(1H,q), 4.18(2H,s), 5.27 (2H,s), 7.00(2H,t), 7.12–7.22(5H,m), 7.38–7.44(1H,m), 7.60(2H,d), 7.75(2H,d), 8.28(1H, s), 9.00(1H, s).
Example 14-2
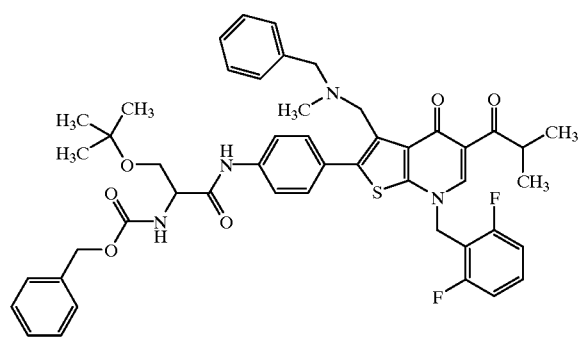
Yield: 47% mp 145–150° C.
Example 14-3
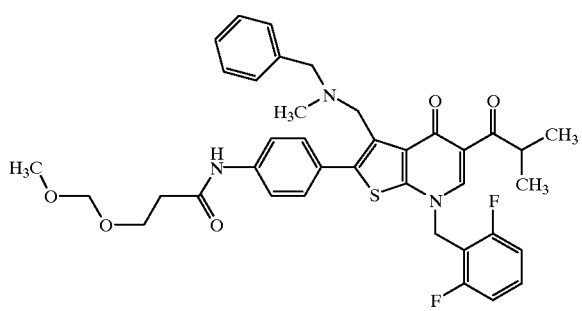
Yield: 99% mp 96–98° C.
Example 14-4
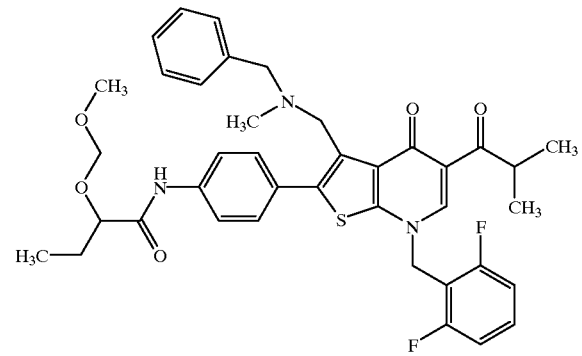
Yield: 57% mp 92–94° C.
Example 14-5
Yield: 71% mp 57–62° C.
Example 14-6
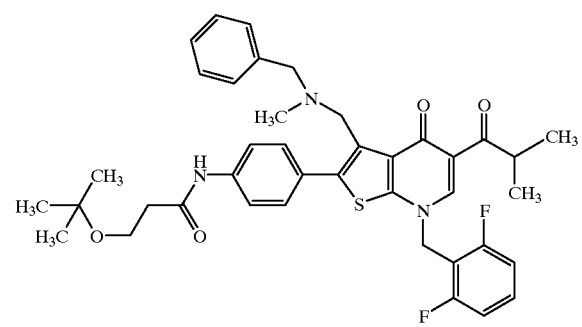
Yield. 92% mp 79–81° C.

Example 14-7
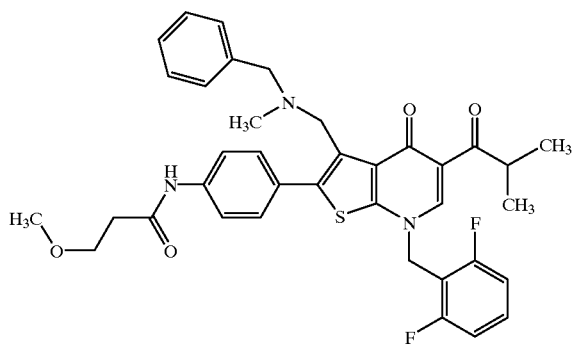
Yield: 97% mp 91–96° C.
Example 14-8
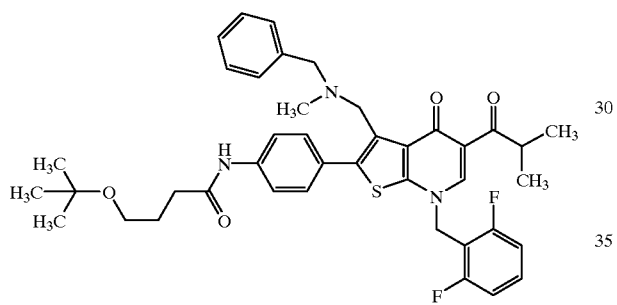
Yield: 91% mp 75–80° C.
Example 14-9
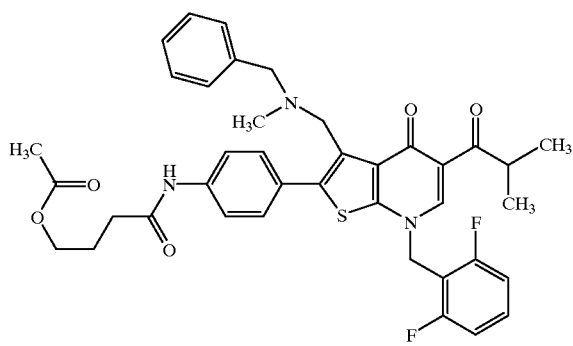
Yield: 87% mp 83–88° C.
Example 14-10
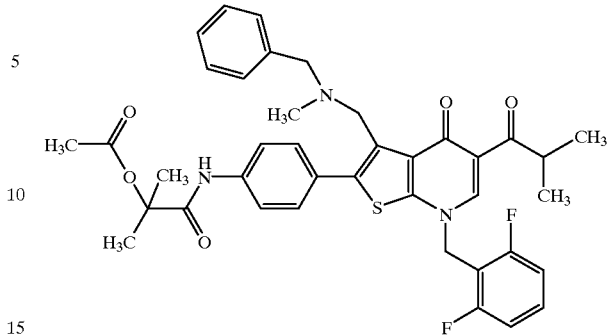
Yield: 50% mp 130–135° C.
Example 15
Using the compound obtained in Example 14, the following compounds (Examples 15-1 to 15-6) in the same manner as in Example 10.
Example 15-1
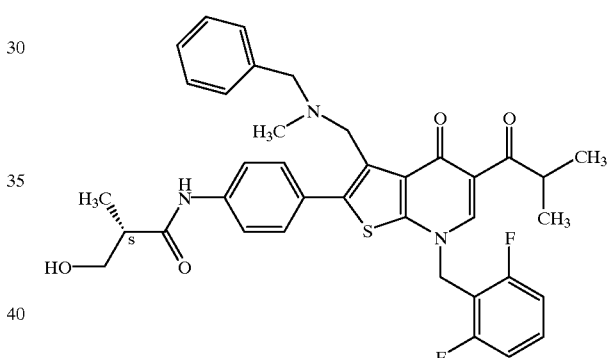
Yield: 69% mp 161–162° C.
Example 15-2
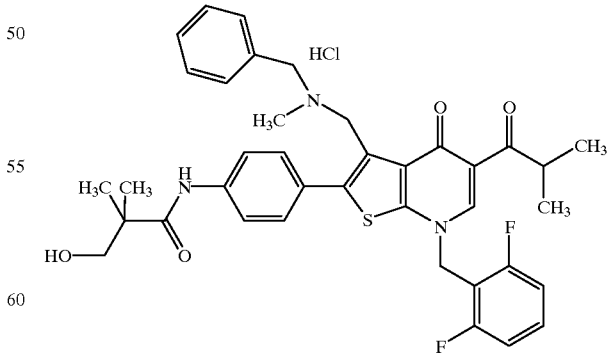
Yield: 94% mp 153–155° C.

Example 15-3

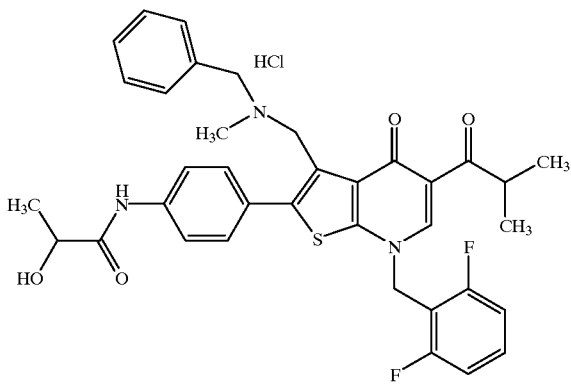

Yield: 62% mp 224–226° C.

Example 15-4

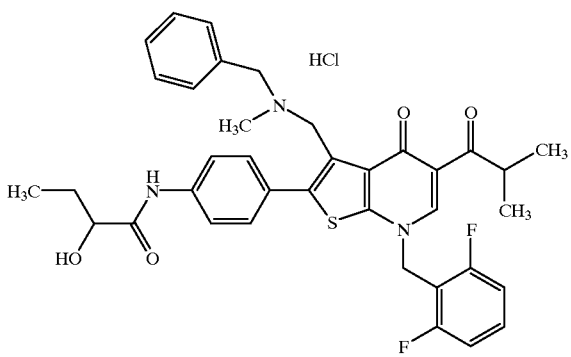

Yield: 56% mp 230–232° C.

Example 15-5

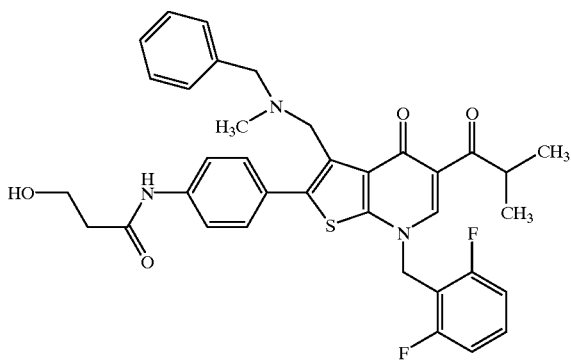

Yield: 90% mp 92–94° C.

Example 15-6

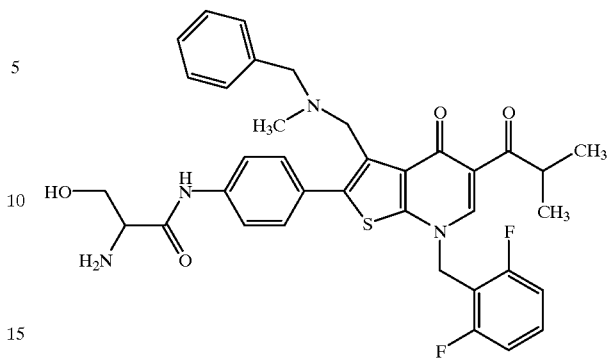

Yield: 34% mp 107–112° C.

Example 16

Example 16-1

Production of 3-(N-benzyl-N-methylaminomethyl)-4,7-dihydro-5-isobutyryl-7-(2,6-difluorobenzyl)-2-(4-N'-methoxyureidophenyl)-4-oxothieno[2,3-b]pyridine

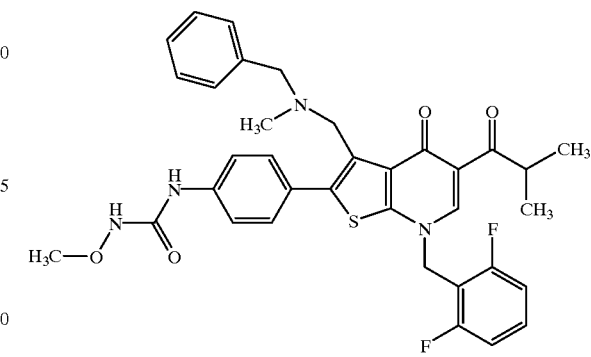

To a solution of the compound obtained in Reference Example 29 (0.40 g, 0.7 mmol) in dichloromethane (15 ml) were added triethylamine (0.20 ml, 1.43 mmol) and N,N'-carbonyldiimidazole (0.228 g, 1.41 mmol), followed by stirring under ice cooling conditions. After the solution was allowed to warm to room temperature and further stirred for 2.5 days, to the mixture were added O-methylhydroxylamine hydrochloride (0.59 g, 7.06 mmol) and triethylamine (0.98 ml, 7.03 mmol) with ice cooling. While the solution was allowed to return to room temperature, it was stirred for 1.5 hours. After dilution with water (50 ml), the reaction mixture was extracted with chloroform (50 ml). The water layer was again extracted with chloroform (10 ml). The combined extracts were washed with saline, and dried ($MgSO_4$), the solvent was distilled off under reduced pressure. The obtained residue was chromatographed on silica gel to yield yellow amorphous powders (0.349 g, 77%).

$^1$H-NMR (300 MHz, $CDCl_3$) δ: 1.19(6H,d), 2.17(3H,s), 3.72(2H,brs), 3.83(3H,s), 4.10–4.20(1H,m), 4.22(2H,brs), 5.28(2H,s), 7.00(2H,t), 7.15–7.24(5H,m), 7.37–7.46(2H,m), 7.59(2H,d), 7.75(2H,d), 7.83(1H, br), 8.31(1H,s).

Example 16-2

Production of 4,7-dihydro-2-(4-N'-methoxyureidophenyl)-7-(2,6-difluorobenzyl)-3-(N-benzyl-N-methylaminomethyl)-5-isobutyryl-4-oxothieno[2,3-b]pyridine hydrochloride

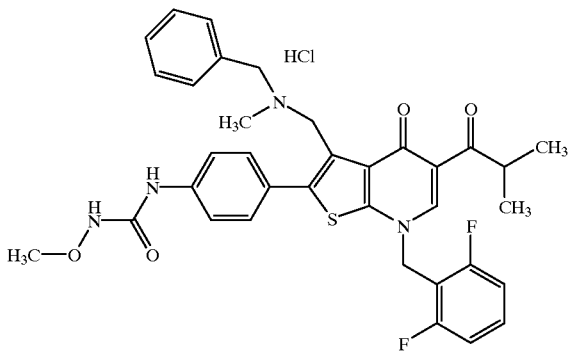

The title compound, white amorphous powders (0.335 g) were obtained in the same manner as in Example 1. Solvent for recrystallization: ethyl acetate-ether mp 225–230° C. Elemental analysis for $C_{35}H_{34}N_4O_4SF_2$·HCl·0.5$H_2O$; C(%), H(%), N(%), Calculated: 60.91; 5.26; 8.12; Found: 60.80; 5.07; 8.17;

Example 17

Example 17-1

Production of (R)-4,7-dihydro-2-[4-(2,3-dihydroxypropionylamino)phenyl]-7-(2,6-difluorobenzyl)-3-(N-benzyl-N-methylaminomethyl)-5-isobutyryl-4-oxothieno[2,3-b]pyridine

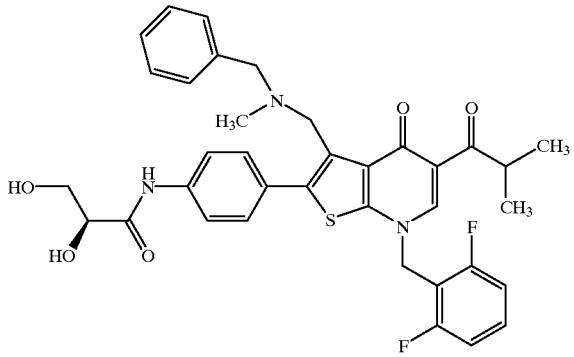

To a 2 N aqueous solution of potassium hydroxide was added (R)-(+)-2,2-dimethyl-1,3-dioxolan-4-carboxylic acid methyl ester (1.00 g, 6.24 mmol), followed by stirring under ice cooling conditions for 3 hours. After neutralization with hydrochloric acid, the solution was salted out and extracted with ethyl acetate (50 ml) to yield (R)-(+)-2,2-dimethyl-1,3-dioxolan-4-carboxylic acid as colorless amorphous powders (0.72 g). To a solution of the compound obtained in Reference Example 29 (0.572 g, 1.0 mmol) in dichloromethane (5 ml) were added diisopropylethylamine (1.04 g, 8 mmol) and the (R)-(+)-2,2-dimethyl-1,3-dioxo-lane-4-carboxylic acid obtained (0.292 g, 2 mmol), followed by stirring under ice cooling conditions. To this solution was added benzotriazol-1-yloxytrisdimethylaminophosphonium hexafluorophosphate (BOP reagent) (0.885 g, 2 mmol). After stirring under ice cooling conditions for 1 hour, the solution was further stirred at room temperature for 4 days. The reaction mixture was concentrated to dryness under reduced pressure, and then the obtained residue was partitioned between water (50 ml) and chloroform (50 ml). The water layer was again extracted with chloroform (10 ml). The combined extracts were washed with saline, and dried (MgSO$_4$), the solvent was distilled off under reduced pressure. The obtained residue was chromatographed on silica gel to yield colorless amorphous powders (0.5 g), which was then dissolved in trifluoroacetic acid (10 ml) and stirred at room temperature for 16 hours. The reaction mixture was concentrated to dryness under reduced pressure and treated with alkali, after which it was partitioned between chloroform (50 ml) and water (50 ml), and then the water layer was again extracted with chloroform (10 ml). The combined extracts were washed with saline, and dried (MgSO$_4$), the solvent was distilled off under reduced pressure. The obtained residue was chromatographed on silica gel to yield 0.5 g of colorless amorphous powders (76%).

$^1$H-NMR (300 MHz, DMSO-d$_6$) δ: 1.09(6H,d), 1.95(3H,s), 3.51(2H,br), 3.55–3.72(2H,m), 4.01–4.08(4H,m), 4.84 (1H,t), 5.63(2H,brs), 5.80(1H,d), 7.15–7.24(7H,m), 7.49–7.57(1H,m), 7.66(2H,d), 7.84(2H,d), 8.53(1H,s), 9.82 (1H,s).

Example 17-2

Production of (R)-4,7-dihydro-2-[4-(2,3-dihydroxypropionylamino)phenyl]-7-(2,6-difluorobenzyl)-3-(N-benzyl-N-methylaminomethyl)-5-isobutyryl-4-oxothieno[2,3-b]pyridine hydrochloride

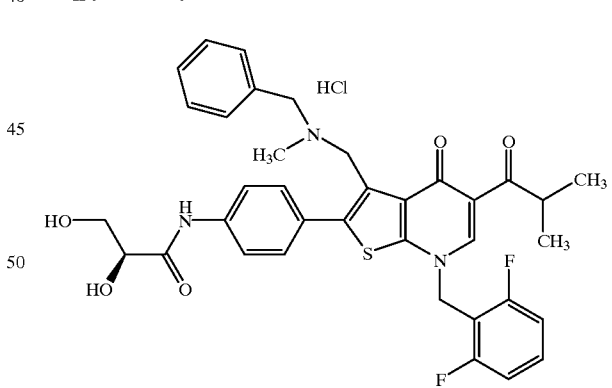

The title compound, white powdery crystals (0.43 g) were obtained in the same manner as in Example 1. Solvent for recrystallization: ether-ethanol mp 146–148° C.

Example 18

Production of 4,7-dihydro-2-(4-N'-hydroxy-N'-methoxyureidophenyl)-7-(2,6-difluorobenzyl)-3-(N-benzyl-N-methylaminomethyl)-5-isobutyryl-4-oxothieno[2,3-b]pyridine

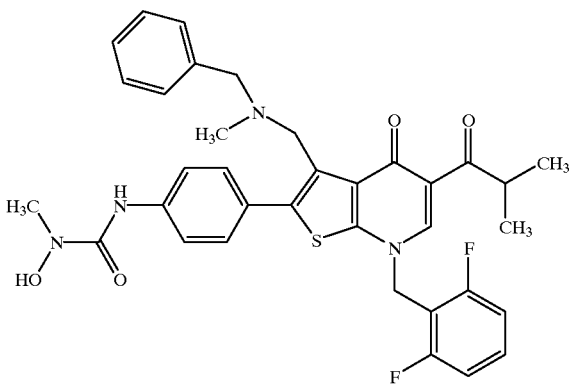

To a solution of the compound obtained in Reference Example 29 (1.0 g, 1.75 mmol) in dichloromethane (40 ml) were added and triethylamine (0.49 ml, 3.50 mmol) and N,N'-carbonyldiumidazole (0.567 mg, 3.50 mmol), followed by stirring under ice cooling conditions. After the solution was allowed to warm to room temperature and further stirred for 17 hours, to the mixture was added N-methylhydroxylammonium chloride (730 mg, 8.75 mmol) and triehylamine (1.23 ml, 8.75 mmol) with ice cooling. While the solution was allowed to warm to room temperature, it was stirred for 5 hours. The reaction mixture was partitioned between chloroform (300 ml) and aqueous sodium bicarbonate (saturated, 200 ml), and then the organic layer was again washed with saline (200 ml). After the organic layer was dried (MgSO$_4$), the solvent was distilled off under reduced pressure. The residue obtained was chromatographed on silica gel to yield pale yellow amorphous powder (0.38 g, 34%).

$^1$H-NMR (300 MHz, CDCl$_3$) δ: 1.18(6H, d), 2.15(3H, s), 3.26(3H, s), 3.71(2H, s), 4.19(2H, s), 5.25(2H, s), 7.00(2H, t), 7.22–7.26(5H, m), 7.41(1H, m), 7.49(2H,d), 7.60(2H,d), 8.06(1H, s), 8.26(1H, s). Elemental analysis for C$_{35}$H$_{34}$N$_4$O$_4$SF$_2$ 0.8H$_2$O; C(%), H(%), N(%), Calculated 63.78; 5.44; 8.50; Found: 63.73; 5.24; 8.41;

Example 19

Production of 2-[4-[(1-acetoxycyclopropyl) carbonylamino]phenyl]-3-(N-benzyl-N-methylaminomethyl)-5-benzoyl-7-(2,6-difluorobenzyl)-4,7-dihydro-4-oxothieno[2,3-b]pyridine

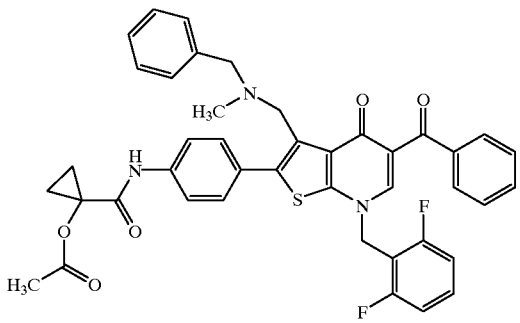

To a solution of the compound obtained in Reference Example 28 (0.42 g, 0.7 mmol) and triethylamine (0.08 g, 0.8 mmol) in dichloromethane (10 ml) was added 1-acetoxycyclopropanecarbonyl chloride (0.13 g, 0.8 mmol) with ice-cooling. The mixture was stirred at 0° C. for 30 minutes and at room temperature for 30 minutes. The reaction mixture was diluted with chloroform (20 ml) and the solution was washed with aqueous sodium bicarbonate (saturated, 20 ml), and brine(20 ml). After the organic layer was dried (Na$_2$SO$_4$), the solvent was distilled off under reduced pressure. The residue obtained was chromatographed on silica gel to yield pale yellow amorphous powders (0.34 g, 66%).

$^1$H-NMR (300 MHz, CDCl$_3$) δ: 1.22(2H, dd), 1.68(2H, dd), 2.12(3H, s), 2.21(3H, s), 3.64(2H, s), 4.13(2H, s), 5.28(2H, s), 7.01(2H, t), 7.17–7.23(5H, m), 7.37–7.44(3H, m), 7.51–7.56(1H, m), 7.60(2H, d), 7.81(2H, d), 7.87–7.90 (3H, m), 7.94(1H,S). FAB-Mass m/z 732 (MH)$^+$ Example 20

Using the compound obtained in Reference Example 28, the following compound Examples 20-1 was obtained in the same manner as in Example 19

Example 20-1

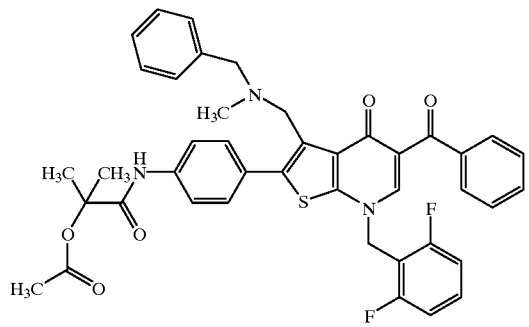

Yield 80%

$^1$H-NMR (300 MHz, CDCl$_3$) δ: 1.77(6H, s), 2.12(3H, s), 2.17(3H, s), 3.63(2H, s), 4.13(2H, s), 5.29(2H, s), 7.01(2H, t), 7.15–7.23(5H, m), 7.38–7.45(3H, m), 7.51–7.56(1H, m), 7.64(2H, d), 7.85(2H, d), 7.88–7.90(3H, m), 7.94(1H, s). FAB-Mass m/z 734(MH)$^+$ Using the compound obtained in Reference Example 28, the following compound Examples 20-2 was obtained in the same manner as in Example 19

Example 20-2

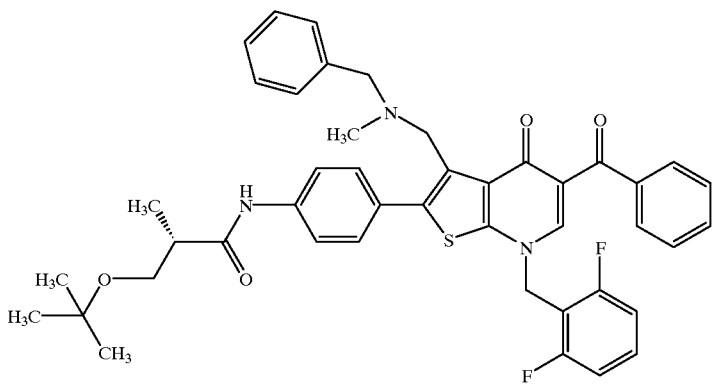

Yield: 84%

1H-NMR (300 MHz, CDCl$_3$) δ: 1.25(3H, d), 1.30(9H, s), 2.10(3H, s), 2.65–2.67(1H, br m), 3.51(2H, t), 3.60(2H, s), 4.12(2H, s), 5.28(2H, s), 7.00(2H, t), 7.16–7.23(5H, m), 7.37–7.42 (3H, m), 7.50–7.53(1H, m), 7.61(2H, d), 7.80(2H, d), 7.89(2H, d), 7.94(11H, s), 9.01(1H, s). FAB-Mass m/z 748(MH)$^+$

Example 21

Production of 3-(N-benzyl-N-methylaminomethyl)-5-benzoyl-7-(2,6-difluorobenzyl)-4,7-dihydro-2-[4-[(1-hydroxy cyclopropyl)carbonylamino]phenyl]-4-oxothieno[2,3-b]pyridine

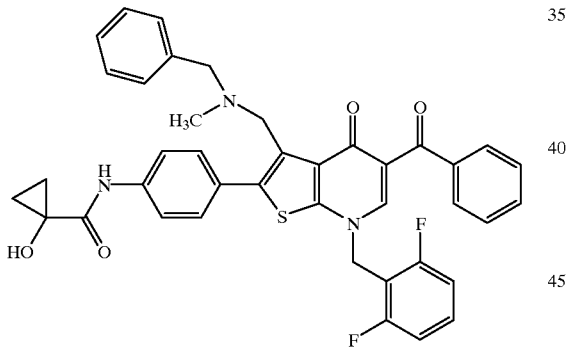

A mixture of the compound obtained in Example 19 (0.24 g, 0.33 mmol) and 5N sodium hydroxide (0.07 ml) in ethanol (8 ml) was stirred at room temperature for 1 hour. After the solvent was distilled off under reduced pressure, the residue obtained was dissolved in chloroform (30 ml) and the solution was washed with aqueous sodium bicarbonate (saturated, 20 ml) and brine(20 ml). After the organic layer was dried (Na$_2$SO$_4$), the solvent was distilled off under reduced pressure and the residue obtained was recrystallized from chloroform-ether to yield pale yellow powders (0.17 g, 75%). mp 186–188° C.

1H-NMR (300 MHz, CDCl$_3$) δ: 1.15(2H, dd), 1.44(2H, dd), 2.05(3H, s), 3.56(2H, s), 4.01(2H, s), 4.56(1H, br s), 5.24(2H, s), 7.00(2H, t), 7.14–7.22(5H, m), 7.41(3H, t), 7.55(2H, d), 7.55(1H, s), 7.70(2H, d), 7.88(2H, d), 7.90(1H, S) 8.88(1H, s). Elemental analysis for C$_{40}$H$_{33}$N$_3$O$_4$SF$_2$ 1.0H$_2$O; C(%), H(%), N(%), Calculated: .67.88; 4.98; 5.94; Found: 67.75; 4.70; 5.90; FAB-Mass m/z 690 (MH)$^+$

Example 22

Production of 3-(N-benzyl-N-methylaminomethyl)-5-benzoyl-7-(2,6-difluorobenzyl)-4,7-dihydro-2-[4-(2-hydroxy-2-methylpropionylamino)phenyl]-4-oxothieno[2,3-b]pyridine

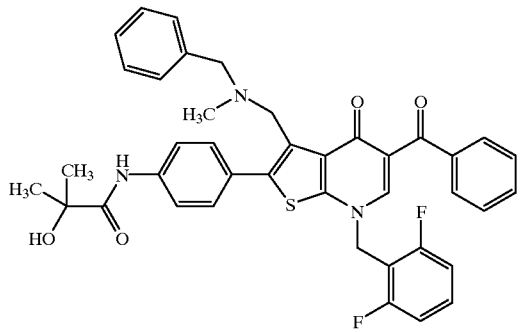

Using the compound obtained in Example 20-1, the title compound was obtained in the same manner as in Example 21. Solvent for recrystallization: chloroform-ether mp 222–223° C. 1H-NMR (300 MHz, CDCl$_3$) δ: 1.57(6H, s), 2.09(3H, s), 2.50(1H, s), 3.59(2H, s), 4.10(2H, s), 5.28 (2H, s), 7.01(2H, t), 7.16–7.25(5H, m), 7.38–7.44(3H, m), 7.51–7.56(1H, m), 7.67(2H, d), 7.82(2H, d), 7.89(2H, d), 7.93(1H, s), 8.82(1H, s). FAB-Mass m/z 692 (MH)$^+$

Example 23

Production of (R)-3-(N-benzyl-N-methylaminomethyl)-5-benzoyl-7-(2,6-difluorobenzyl)-4,7-dihydro-2-[4-[(3-hydroxy-2-methylbutyryl amino)phenyl]-4-oxothieno2,3-b]pyridine

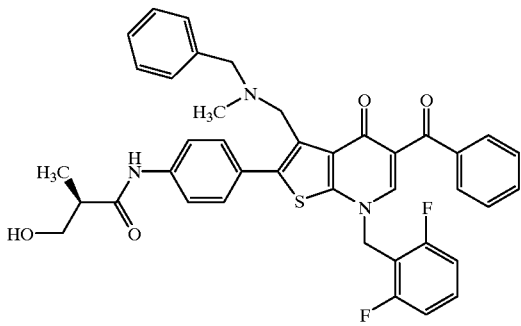

Using the compound obtained in Example 20-2, the title compound was obtained in the same manner as in Example 10. Solvent for recrystallization: chloroform-ether mp 145–146° C.

$^1$H-NMR (300 MHz, CDCl$_3$) δ: 1.25(3H, d), 2.07(3H, s), 2.63–2.70(1H, m), 2.84(1H, br s), 3.57(2H, s), 3.78–3.81 (2H, m), 4.08(2H, s), 5.27(2H, s), 7.00(2H, t), 7.17–7.20 (5H, m), 7.37–7.43(3H, m), 7.51–7.56(1H, m),7.61(2H, d), 7.77(2H, d), 7.89(2H, d), 7.94(1H, s), 8.31(1H, br s).

FAB-Mass m/z 692 (MH)$^+$

Preparation Example 1

Using 100 mg of the compound produced in Example 1-2, 165 mg of lactose, 25 mg of corn starch, 4 mg of polyvinyl alcohol and 1 mg of magnesium stearate, tablets are produced by a conventional method.

Preparation Example 2

The compound produced in Example 1-2 (5 g) is dissolved in distilled water for injection to make a total volume of 100 ml. This solution is aseptically filtered through a 0.22 μm membrane filter (produced by Sumitomo Electric Industries, Ltd. or Sartorius) and dispensed at 2 ml per washed sterile vial, followed by freeze-drying by a conventional method, to yield a 100 mg/vial freeze-dried injectable preparation.

Preparation Example 3

Using 100 mg of the compound produced in Example 3, 165 mg of lactose, 25 mg of corn starch, 4 mg of polyvinyl alcohol and 1 mg of magnesium stearate, tablets are produced by a conventional method.

Preparation Example 4

The compound produced in Example 3 (5 g) is dissolved in distilled water for injection to make a total volume of 100 ml. This solution is aseptically filtered through a 0.22 μm membrane filter (produced by Sumitomo Electric Industries, Ltd. or Sartorius) and dispensed at 2 ml per washed sterile vial, followed by freeze-drying by a conventional method, to yield a 100 mg/vial freeze-dried injectable preparation.

Preparation Example 5

| (1) Compound produced in Example 1–2 | 5 g |
|---|---|
| (2) Lactose/crystalline cellulose (particles) | 330 g |
| (3) D-mannitol | 29 g |
| (4) Low-substitutional hydroxypropyl cellulose | 20 g |
| (5) Talc | 25 g |
| (6) Hydroxypropyl cellulose | 50 g |
| (7) Aspartame | 3 g |
| (8) Dipotassium glycyrrhizinate | 3 g |
| (9) Hydroxypropylmethyl cellulose 2910 | 30 g |
| (10) Titanium oxide | 3.5 g |
| (11) Yellow iron sesquioxide | 0.5 g |
| (12) Light silicic anhydride | 1 g |

Components (1), (3), (4), (5), (6), (7) and (8) are suspended or dissolved in purified water and coated on the core particles (2) to yield base fine subtilae, which are then further coated with components (9) through (11) to yield coated fine subtilae, which are then mixed with component (12) to yield 500 g of 1% fine subtilae of the compound. These subtilae are divided to 500 mg folded subtilae.

Experimental Example 1

Preparation of $^{125}$I-leuprorelin

To a tube containing 10 μl of a 3×10$^{-4}$ M aqueous solution of leuprorelin and 10 μl of 0.01 mg/ml lactoperoxidase, 10 μl (37 MBq) of a solution of Na$^{125}$I was added. After stirring, 10 μl of 0.001% H$_2$O$_2$ was added, and a reaction was carried out at room temperature for 20 minutes. By adding 700 μl of a 0.05% TFA (trif luoroacetic acid) solution, the reaction was stopped, followed by purification by reversed-phase HPLC. The HPLC conditions used are shown below. $^{125}$I-leuprorelin was eluted at a retention time of 26 to 27 minutes. Column: TSKgel ODS-$_{80}$™ (TM indicates a registered trademark: the same applies below) CTR (4.6 mm×10 cm) Eluents: Solvent A (0.05% TFA)

Solvent B (40% CH$_3$CN-0.05% TFA)

0 minute (100% Solvent A)-3 minutes (100% Solvent A)-7 minutes (50% Solvent A+50% Solvent B)-40 minutes (100% Solvent B)

Eluting temperature: Room temperature Elution rate: 1 ml/min

Experimental Example 2

Preparation of a rat pituitary anterior lobe membrane fraction containing GnRH receptors Anterior lobes of the pituitary glands were isolated from forty Wistar rats (8 weeks old, male), and washed with ice-cooled homogenate buffer [25 mM Tris (tris (hydroxymethyl)amino methane)-HCl, 0.3 M sucrose, 1 mM EGTA (glycol-ether diamine-N,N,N',N'-tetra acetic acid), 0.25 mM PMSF (phenylmethylsulfonyl fluoride), 10 U/ml aprotinin, 1 mg/ml pepstatin, 20 mg/ml leupeptin, 100 mg/ml phosphoramidon, 0.03% sodium azide, pH 7.5]. The pituitary tissue was floated in 2 ml of the homogenate buffer and homogenized using a Polytron homogenizer. The homogenate was centrifuged at 700×g for 15 minutes. The supernatant was taken in an ultra centrifuge tube and centrifuged at 100,000×g for 1 hour to provide a membrane fraction pellet. This pellet was suspended in 2 ml of assay buffer [25 mM Tris-HCl, 1 mM EDTA (ethylenediaminetetraacetic acid), 0.1% BSA (bovine serum albumin), 0.25 mM PMSF, 1 mg/ml pepstatin, 20 mg/ml leupeptin, 100 mg/ml phosphoramidon, 0.03% sodium azide, pH 7.5) and the suspension was centrifuged at 100,000×g for 1 hour. The membrane fraction recovered as a pellet was resuspended in 10 ml of assay buffer, divided into portions, preserved at −80° C. and thawed when needed.

Experimental Example 3

Preparation of CHO (Chinese hamster ovarian) cell membrane fraction containing human GnRH receptor Human GnRH receptor-expressing CHO cells (EP-A-678577) ($10^9$ cells) were suspended in phosphate-buffered saline supplemented with 5 mM EDTA (ethylenediaminetetraacetic acid) (PBS-EDTA) and centrifuged at 100×g for 5 minutes. To the cell pellet, 10 ml of a cell homogenate buffer (10 mM $NaHCO_3$, 5 mM EDTA, pH 7.5) was added, followed by homogenization using the Polytron homogenizer. After centrifugation at 400×g for 15 minutes, the supernatant was transferred to an ultra centrifugation tube and centrifuged at 100,000×g for 1 hour to yield a membrane fraction precipitate. This precipitate was suspended in 2 ml of an assay buffer and centrifuged at 100,000×g for 1 hour. The membrane fraction recovered as a precipitate was again suspended in 20 ml of the assay buffer, dispensed, and stored at −80° C. before use upon thawing.

Experimental Example 4

Determination of $^{125}$I-leuprorelin binding inhibition rate

The rat and human membrane fractions prepared in Experimental Examples 2 and 3 were diluted with the assay buffer to yield a 200 mg/ml dilution, which was then dispensed at 188 ml per tube. Where the rat pituitary anterior lobe membrane fraction was used, to each tube, 2 ml of a solution of 0.1 mM compound in 601 DMSO (dimethyl sulfoxide) and 10 µl of 38 nM $^{125}$I-leuprorelin were added simultaneously. Where the cell membrane fraction of the CHO with human GnRH receptors expressed, to each tube, 2 ml of a solution of 2 mM compound in 60% DMSO and 10 µl of 38 nM $^{125}$I-leuprorelin were added simultaneously. To determine maximum binding quantity, a reaction mixture of 2 µl of 60% DMSO and 10 µl of 38 nM $^{125}$I-leuprorelin was prepared. To determine non-specific binding amount, a reaction mixture of 2 µl of 100 µM leuprorelin in solution in 60% DMSO and 10 µl of 38 nM $^{125}$I-leuprorelin was prepared.

Where the rat or bovine pituitary anterior lobe membrane fraction was used, the reaction was conducted at 4° C. for 90 minutes. Where the membrane fraction of the CHO with human GnRH receptors expressed was used, the reaction was carried out at 25° C. for 60 minutes. After each reaction, the reaction mixture was aspirated and filtered through a polyethyleneimine-treated What man glass filter (GF-F). After this filtration, the radioactivity of $^{125}$I-leuprorelin remaining on the filter paper was measured with a γ-counter. The expression (TB-SB)/(TB-NSB)×100 (where SB=radioactivity with the compound added, TB=maximum bound radioactivity, NSB=nonspecifically bound radioactivity) was calculated to find the binding inhibition rate (%) of each test compound. Furthermore, the inhibition rate was determined by varying the concentration of the test substance and the 50% inhibitory concentration ($IC_{50}$ value) of the compound was calculated from Hill plot. The results are shown in below.

| Test Compound | binding inhibition rate (%) | | $IC_{50}$ value (µM) | |
|---|---|---|---|---|
| | Rat (1 µM) | Human (20 µM) | Rat | Human |
| Compd. of Ex. 1–2 | 96 | 102 | 0.06 | 0.0001 |
| Compd. of Ex. 3 | 62 | NT | 0.6 | 0.0002 |

NT: not measured

Experimental Example 5

Suppression of blood LH in castrated monkeys

The compound produced in Example 1-2 was orally administered to castrated male cynomolgus monkeys (Macaca fascicularis), and blood LH was quantified. The male cynomolgus monkeys, used at 3 years 8 months to 7 years 7 months of age at time of experimentation, had been castrated more than half a year prior to the examination. Test animals [n=2; compound (1) and compound (2)] were given 30 mg/kg (3 ml/kg) of the compound suspended in 0.5% methyl cellulose at a final concentration of 1% by oral administration, and control animals (n=3; control (1), control (2) and control (3)] were given 3 ml/kg of the 0.5% methyl cellulose dispersant alone by oral administration. At 24 hours and immediately before administration and at 2, 4, 6, 8, 24, and 48 hours after administration, blood was collected for heparinized plasma samples via the femoral vein and immediately stored under freezing conditions.

Plasma LH concentrations were determined by a bioassay using mouse testicular cells. The testicular cells were collected from male BALB/c mice (8 to 9 weeks of age) and washed three times with 1 ml of Dulbecco's modified Eagle medium (DMEM-H) containing 20 mM HEPES and 0.2% BSA per testis. After incubation at 37° C. for 1 hour, the cells were passed through a nylon mesh filter (70 µm) and dispensed to test tubes at $8 \times 10^5$ cells/tube. After the cells were washed twice with 0. 4 ml of DMEM-H, 0.4 ml of a DMEM-H solution containing either equine LH (Sigma Company), as the standard LH, or monkey plasma, previously diluted up to 1,000 fold, as the test sample, was added, followed by a reaction at 37° C. for 2 hours. The testosterone concentration in the culture supernatant was determined by a radioimmunoassay (CIS Diagnostics Company), and the LH concentration in the test monkey plasma was calculated from the standard curve for the standard equine LH.

The results are given together in FIG. 1.

The compound indicated is the compound obtained in Example 1-2.

For the control (1), the control (2), and the control (3), changes over time in the LH concentrations in each animal are expressed as percent ratios to the respective reference values, which comprise the LH concentrations immediately before administration in each control animal (cynomolgus monkey). Similarly, for the compound (1) and the compound (2), changes over time in the LH concentrations in each animal (cynomolgus monkey) receiving the compound of Example 1-2 are expressed as percent ratios to the respective reference values, which comprise the LH concentrations immediately before administration of the compound. The time of administration was defined as zero (0), and hours before and after administration shown by minus and plus, respectively.

INDUSTRIAL APPLICABILITY

The compound of the present invention possesses excellent gonadotropin-releasing hormone antagonizing activity. It is also good in oral absorbability and excellent in stability and pharmacokinetics. With low toxicity, it is also excellent in safety.

The compound of the present invention can therefore be used as a prophylactic or therapeutic agent for hormone-dependent diseases etc. Specifically, it is effective as a prophylactic or therapeutic agent for sex hormone-dependent cancers (e.g., prostatic cancer, uterine cancer, breast cancer, pituitary tumor), prostatic hypertrophy, hysteromyoma, endometriosis, precocious puberty, amenorrhea syndrome, multilocular ovary syndrome, pimples etc, or as a pregnancy regulator (e.g., contraceptive), infertility remedy or menstruation regulator. It is also effective as an animal estrous regulator, food meat quality improving agent or animal growth regulator in the field of animal husbandry, and as a fish spawning promoter in the field of fishery.

What is claimed is:

1. A compound of the formula:

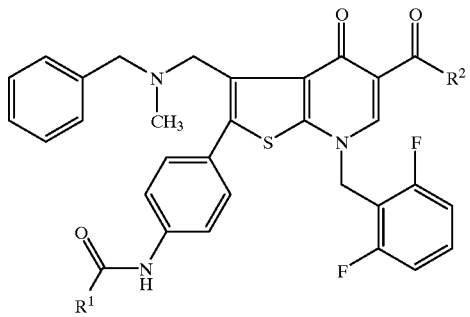

wherein $R^1$ represents a $C_{1-7}$ alkyl group substituted by 1 to 5 substituents selected from the group consisting of (i) hydroxy, (ii) $C_{1-7}$ acyloxy, (iii) amino which may be substituted by 1 or 2 substituents selected from the group consisting of $C_{1-6}$ alkoxy-carbonyl, benzyloxycarbonyl, $C_{1-3}$ acyl, $C_{1-3}$ alkylsulfonyl and $C_{1-3}$ alkyl, (iv) $C_{1-10}$ alkoxy which may be substituted by 1 to 3 substituents selected from the group consisting of $C_{3-7}$ cycloalkyloxy-carbonyl and $C_{1-3}$ alkoxy and (v) $C_{1-6}$ alkoxy-carbonyl; and $R^2$ represents a $C_{1-7}$ alkyl group which may be substituted or a phenyl group which may be substituted, or a salt thereof.

2. A compound of claim 1 or a salt thereof, wherein $R^2$ is (1) a $C_{1-7}$ alkyl group which may be substituted by 1 to 5 substituents selected from the group consisting of (i) hydroxy, (ii) $C_{1-7}$ acyloxy, (iii) amino which may be substituted by 1 or 2 substituents selected from the group consisting of $C_{1-6}$ alkoxy-carbonyl, benzyloxycarbonyl, $C_{1-3}$ acyl, $C_{1-3}$ alkylsulfonyl and $C_{1-3}$ alkyl, (iv) $C_{1-10}$ alkoxy which may be substituted by 1 to 3 substituents consisting of $C_{3-7}$ cycloalkyloxy-carbonyl and $C_{1-3}$ alkoxy, and (v) $C_{1-6}$ alkoxy-carbonyl, or (2) a phenyl group which may be substituted by 1 to 5 substituents selected from the group consisting halogen, $C_{1-3}$ alkyl and $C_{1-3}$ alkoxy.

3. A compound of claim 1 or a salt thereof, wherein $R^1$ is a $C_{1-7}$ alkyl group substituted by hydroxy.

4. A compound of claim 1 or a salt thereof, wherein $R^2$ is a branched $C_{3-7}$ alkyl group which may be substituted.

5. A compound of claim 1 or a salt thereof, wherein $R^2$ is a phenyl group which may be substituted.

6. A compound of claim 1 or a salt thereof, wherein $R^2$ is a phenyl group.

7. A compound of claim 1 or a salt thereof, wherein $R^1$ is a $C_{1-4}$ alkyl group substituted by 1 or 2 hydroxy; and $R^2$ is an isopropyl group or a phenyl group.

8. A compound of claim 1 or a salt thereof, wherein $R^1$ is a $C_{1-7}$ alkyl group substituted by 1 or 2 substituents selected from the group consisting of hydroxy, $C_{1-3}$ alkylcarbonyloxy, amino, benzyloxycarbonylamino, $C_{1-3}$ alkoxy, $C_{1-3}$ alkoxy-$C_{1-3}$ alkoxy and $C_{1-3}$ alkoxy-carbonyl; and $R^2$ is (1) an isopropyl group which may be substituted by a hydroxy or (2) a phenyl group.

9. 3-(N-Benzyl-N-methylaminomethyl)-4,7-dihydro-5-isobutyryl-7-(2,6-difluorobenzyl)-2-[4-(3-hydroxy-2-methylpropionylamino)phenyl]-4-oxothieno[2,3-b]pyridine or a salt thereof.

10. A process for producing a compound of claim 1 or a salt thereof, which comprises reacting a compound of the formula:

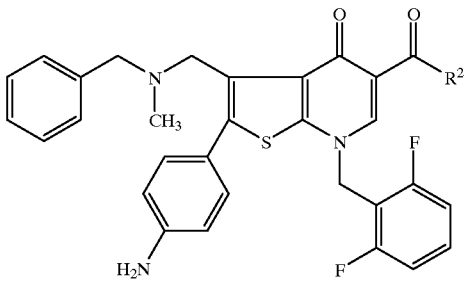

wherein $R^2$ represents a $C_{1-7}$ alkyl group which may be substituted or a phenyl group which may be substituted, or a salt thereof, with a compound of the formula:

$R^{1a}COOH$ wherein $R^{1a}$ represents a $C_{1-7}$ alkyl group substituted by 1 to 5 substituents selected from the group consisting of (i) hydroxy, (ii) $C_{1-7}$ acyloxy, (iii) amino which may be substituted by 1 or 2 substituents selected from the group consisting of $C_{1-6}$ alkoxy-carbonyl, benzyloxycarbonyl, $C_{1-3}$ acyl, $C_{1-3}$ alkylsulfonyl and $C_{1-3}$ alkyl, (iv) $C_{1-10}$ alkoxy which may be substituted by 1 to 3 substituents selected from the group consisting of $C_{3-7}$ cycloalkyloxy-carbonyl and $C_{1-3}$ alkoxy, and (v) $C_{1-6}$ alkoxy-carbonyl, or a salt thereof.

11. A pharmaceutical composition which comprises a compound of claim 1 or a salt thereof and a pharmaceutically acceptable carrier or excipient.

12. A method for antagonizing gonadotropin-releasing hormone in a mammal in need thereof, said method comprising administering an effective amount of a pharmaceutical composition of claim 11 to said mammal.

13. A method treating a sex hormone dependent disease in a mammal in need of such treatment, said method comprising administering an effective amount of a pharmaceutical composition of claim 11 to said mammal.

14. A method for antagonizing gonadotropin-releasing hormone in a mammal in need thereof which comprises administering to said mammal an effective amount of a compound of claim 1 or a salt thereof.

15. A method for manufacturing a pharmaceutical composition, said method comprising combining a compound of claim 1 or a salt thereof with a pharmaceutically acceptable carrier or excipient.

16. (R)-4,7-dihydro-2-[4-(2,3-dihydroxypropionylamino)phenyl]-7-(2,6-difluorobenzyl)-3-(N-benzyl-N-methylaminomethyl)-5-isobutyryl-4-oxothieno[2,3-b]pyridine or a salt thereof.

17. (R)-4,7-dihydro-2-[4-(2,3-dihydroxypropionylamino)phenyl]-7-(2,6-difluorobenzyl)-3-(N-benzyl-N-methylaminomethyl)-5-isobutyryl-4-oxothieno[2,3-b]pyridine hydrochloride.

* * * * *

UNITED STATES PATENT AND TRADEMARK OFFICE
CERTIFICATE OF CORRECTION

PATENT NO.    : 6,329,388 B1
DATED         : December 11, 2001
INVENTOR(S)   : Miki, Shokyo and Fukuoka, Koichiro It is certified that error appears in the above-identified patent and that said Letters Patent is hereby corrected as shown below:

Column 1,
Line 9, "PCT/JP99/033790" should read -- PCT/JP99/03379 --

Column 31,
Line 12, in the structure of Reference Example 31-9 "$CF_2CH_2O$" should read -- $CF_3CH_2O$ --

Column 64,
Line 45, "A method treating" should read -- A method for treating --

Signed and Sealed this

Ninth Day of July, 2002

Attest:

JAMES E. ROGAN
Attesting Officer        Director of the United States Patent and Trademark Office